(12) United States Patent
Iwakuma

(10) Patent No.: US 7,662,487 B2
(45) Date of Patent: Feb. 16, 2010

(54) AZAAROMATIC COMPOUNDS HAVING AZAFLUORANTHENE SKELETONS AND ORGANIC ELECTROLUMINESCENT DEVICES MADE BY USING THE SAME

(75) Inventor: Toshihiro Iwakuma, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 152 days.

(21) Appl. No.: 11/931,374

(22) Filed: Oct. 31, 2007

(65) Prior Publication Data

US 2008/0206597 A1 Aug. 28, 2008

Related U.S. Application Data

(63) Continuation of application No. PCT/JP2006/317845, filed on Sep. 8, 2006.

(30) Foreign Application Priority Data

Sep. 9, 2005 (JP) .............................. 2005-262288

(51) Int. Cl.
*H01L 51/54* (2006.01)
*C07D 241/36* (2006.01)
*C07D 495/00* (2006.01)
*C09K 11/00* (2006.01)

(52) U.S. Cl. ...................... 428/690; 428/917; 313/504; 313/506; 544/338; 544/339; 544/342; 544/343

(58) Field of Classification Search .................. None
See application file for complete search history.

(56) References Cited

U.S. PATENT DOCUMENTS 6,917,159 B2 * 7/2005 Tyan et al. .................. 313/506

FOREIGN PATENT DOCUMENTS

| JP | 2-216791 | 8/1990 |
|----|----------|--------|
| JP | 4-363891 | 12/1992 |
| JP | 7-41759 | 2/1995 |
| JP | 7-90260 | 4/1995 |
| JP | 9-13025 | 1/1997 |
| JP | 10-189247 | 7/1998 |
| JP | 11-12205 | 1/1999 |
| JP | 2000-311786 | 11/2000 |
| JP | 2001-160489 | 6/2001 |
| JP | 2003-212875 | 7/2003 |
| JP | 3571977 | 7/2004 |
| JP | 3614405 | 11/2004 |
| JP | 2005-68367 | 3/2005 |
| JP | 2005-514739 | 5/2005 |
| JP | 3794819 | 4/2006 |

OTHER PUBLICATIONS

Machine-generated translation for JP 2001-160489 published Jun. 2001.*
Machine-generated translation for JP 2003-212875 published Jul. 2003.*
Machine-generated translation for JP 2005-068367 published Mar. 2005.*
Chérif F. Matta, et al., "Characterization of a Closed-Shell Fluorine-Fluorine Bonding Interaction in Aromatic Compounds on the Basis of the Electron Density", J. Phys. Chem. A, vol. 109, No. 16, Apr. 28, 2005, pp. 3669-3681.
J. Burdon, et al., "Polycyclic Fluoroaromatic Compounds—IV[1] some Reactions of Octafluoroacenaphthylene", Tetrahedron, vol. 21, No. 5, May 1965, pp. 927-936.
Frank B. Mallory, et al., "Nuclear Spin-Spin Coupling via Nonbonded Interactions. 8. The Distance Dependence of Through-Space Fluorine-Fluorine Coupling", J. Am. Chem. Soc., vol. 122, No. 17, May 3, 2000, pp. 4108-4116.
Hans W. Rothkopf, et al., "Di-und Tetracyanpyrazine", Chem. Ber., vol. 108, No. 3, 1975, pp. 875-886.
Tai-Hsiang Huang, et al., "Tunable Dipolar Acenaphthopyrazine Derivatives Containing Diphenylamine", Chemistry of Materials. vol. 16, No. 25, Dec. 14, 2004, pp. 5387-5393.
Aleksandar Golubovic, "Photoconductive Properties of Aceanthraquinoxaline and Related Pyrazines", The Journal of Physical Chemistry, vol. 73, No. 5, May 1969, pp. 1352-1356.

* cited by examiner

*Primary Examiner*—Dawn Garrett
(74) *Attorney, Agent, or Firm*—Oblon, Spivak, McClelland, Maier & Neustadt, L.L.P.

(57) ABSTRACT

The invention aims at providing a novel azaaromatic compound having an azafluoranthene skeleton which is useful as the constituent of organic EL devices and at realizing a long lifetime, high-efficiency and practical organic EL device by using the compound in at least one of the organic compound layers. The invention provides azaaromatic compounds having azafluoranthene skeletons as represented by the general formula (1): wherein $R_1$ to $R_{12}$ are each independently hydrogen, substituted or unsubstituted alkyl having 1 to 30 carbon atoms, substituted or unsubstituted alkoxy having 1 to 30 carbon atoms, substituted or unsubstituted aryl having 6 to 40 carbon atoms, trialkylsilyl (wherein each alkyl has 1 to 20 carbon atoms and may be substituted), aryloxy (wherein the aryl has 6 to 40 carbon atoms and may be substituted), halogen atom, or cyano group, with the proviso that at least two of $R_1$ to $R_{12}$ are each cyano group, trifluoromethyl group, or fluorine atom and adjacent two of $R_1$ to $R_{12}$ may be linked together to form a ring structure.

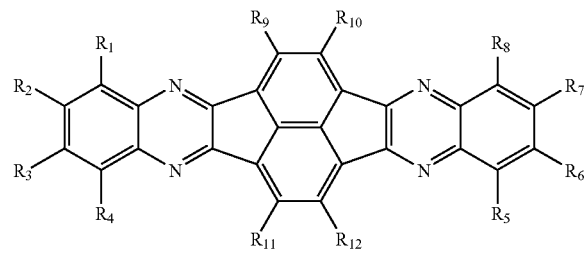

(1)

20 Claims, No Drawings

AZAAROMATIC COMPOUNDS HAVING AZAFLUORANTHENE SKELETONS AND ORGANIC ELECTROLUMINESCENT DEVICES MADE BY USING THE SAME

TECHNICAL FIELD

The present invention relates to a novel azaaromatic compound having an azafluoranthene skeleton, a material for organic electroluminescence (EL) devices which makes use of the azaaromatic compound and an organic electroluminescence (EL) device comprising the material, and more specifically to an azaaromatic compound having an azafluoranthene skeleton, which is useful as an constituent of an organic EL device and a material for organic EL devices which makes use of the azaaromatic compound as well as a highly efficient and practically applicable organic EL device in which at least one of organic layers comprises the azaaromatic compound having an azafluoranthene skeleton, and which has a long lifetime.

BACKGROUND ART

The organic electroluminescence (EL) device using organic material has been considered to be hopeful for use as a solid emitting type full color display device, which is cheap and has a large area and accordingly, there have widely been conducted a variety of investigations for the development of such devices. In general, the EL device comprises a emitting layer and a pair of electrodes interposing the emitting layer between them. The emission of light from the EL device is such a phenomenon that, when an electric field is applied between these electrodes, electrons are injected into the emitting layer from the side of the cathode, while holes are likewise injected into the layer from the side of the anode, subsequently the electrons are recombined with the holes within the emitting layer to generate excited states and energies are converted in the form of light when the excited states are brought back to the ground states.

Recently, the techniques relating to the organic EL device have made a considerable progress. The organic EL device can be characterized in that it can be formed into a thin and light-weight emitting device which has a high-luminance even when applying a low voltage and a wide range of luminous wavelengths, and which device can respond at a high speed and thus said characteristics suggest a wide range of possible applications of the organic EL device.

However, the organic EL device at present is needed to have a higher luminance of a light output or higher conversion efficiency. In addition, the existing organic EL device has still suffered from a variety of problems concerning the durability such as a change of in characteristics with time when using the device over a long period of time deterioration due to an atmospheric gas containing oxygen or a moisture. Furthermore, the EL device should emit blue, green, and red light excellent in the purity of color when taking into consideration the application thereof to the full color display devices or the like, but this problem has not yet been solved satisfactorily.

JP2005-514739A discloses an example in which a compound having a dibenzoquinoxaline skeleton is used as a material for a hole blocking layer (electron transporting layer) and an emitting material. However, this patent application does not sufficiently disclose the characteristic properties of the device and accordingly, the effect accomplished by the device is vague.

Japanese Patent No. 3,571,977 discloses an organic EL device which makes use of a hexaazatriphenylene derivative as a material for an electron injecting layer. This EL device is improved in the electron injecting properties, but the improvement has not yet been sufficient.

Moreover, there have been known, as materials for electron injecting layers, oxadiazole derivatives such as those disclosed in, for instance, Japanese Un-Examined Patent Publication (Hereunder simply referred to as "J.P. KOKAI") Nos. Hei 2-216791 and Hei 4-363891; and triazine derivatives such as those disclosed in, for instance, J.P. KOKAI Nos. Hei 7-41759 and Hei 7-90260. However, the organic emitting devices prepared using these materials have still been insufficient in their stability of films, and their electron injection efficiencies and thus these devices have still been insufficient in the luminance of the emitted light and the lifetime.

Japanese Patent No. 3,614,405 discloses an organic EL device which comprises hexaazatriphenylene derivative having 6 cyano substituents. When this compound is used in the hole injecting layer, the resulting device is improved in the hole injecting property and said improvement contributes to the reduction of the operating voltage of the device. However, since the intermolecular interaction due to polar functional groups is too strong, the vapor deposition temperature of the compound becomes high and thus there is concern that the compound may undergo decomposition.

[Patent Document 1] JP2005-514739A;
[Patent Document 2] Japanese Patent No. 3,571,977;
[Patent Document 3] J.P. KOKAI Hei 2-216791;
[Patent Document 4] J.P. KOKAI Hei 4-363891;
[Patent Document 5] J.P. KOKAI Hei 7-41759;
[Patent Document 6] J.P. KOKAI Hei 7-90260;
[Patent Document 7] Japanese Patent No. 3,614,405.

DISCLOSURE OF THE INVENTION

Problems That the Invention is to Solve

The invention aims at providing a novel azaaromatic compound having an azafluoranthene skeleton which is useful as the constituent of organic EL devices and at realizing a long lifetime, high-efficiency and practical organic EL device by using the compound in at least one of the organic compound layers.

Means for Solving the Problems

The inventors of this invention have conducted various studies to achieve the foregoing objects, have found that, when a novel azaaromatic compound having an azafluoranthene skeleton having a specific structure is used in at least one of the organic compound-containing layers constituting an organic EL device, the resulting organic EL device shows an extended lifetime and a highly improved efficiency and have thus completed the present invention. More specifically, the present invention herein provides an azaaromatic compound having an azafluoranthene skeleton represented by the following general formula (1):

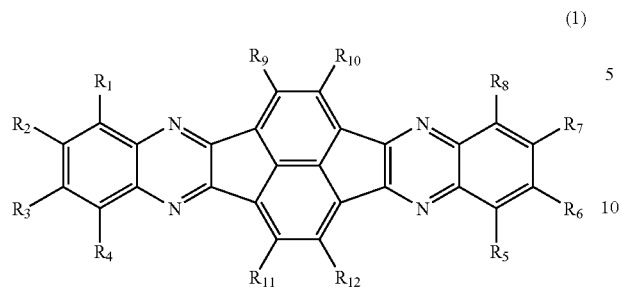

(1)

wherein $R_1$ to $R_{12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{12}$ each represent a cyano group, a trifluoromethyl group or a fluorine atom and that those of $R_1$ to $R_{12}$, which are adjacent to one another, may be linked together to form a ring structure.

According to another aspect of the present invention, there is provided an azaaromatic compound having an azafluoranthene skeleton represented by the following general formula (2):

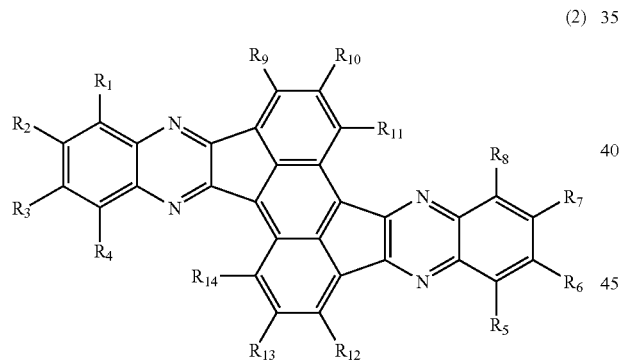

(2)

wherein $R_1$ to $R_{14}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{14}$ each represent a cyano group, a trifluoromethyl group or a fluorine atom and that those of $R_1$ to $R_{14}$, which are adjacent to one another, may be linked together to form a ring structure.

According to still another aspect of the present invention, there is provided an azaaromatic compound having an azafluoranthene skeleton represented by the following general formula (3):

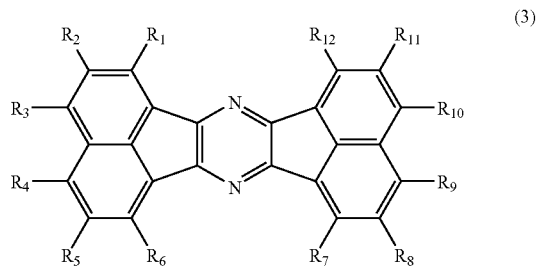

(3)

wherein $R_1$ to $R_{12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{12}$ each represent a cyano group, a trifluoromethyl group or a fluorine atom and that those of $R_1$ to $R_{12}$, which are adjacent to one another, may be linked together to form a ring structure.

According to a further aspect of the present invention, there is provided an azaaromatic compound having an azafluoranthene skeleton represented by the following general formula (4):

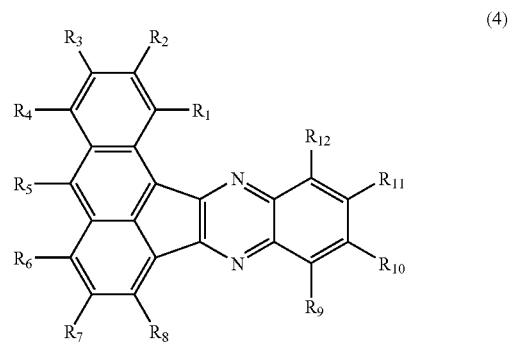

(4)

wherein $R_1$ to $R_{12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{12}$ each represent a cyano group, a trifluoromethyl group or a fluorine atom and that those of $R_1$ to $R_{12}$, which are adjacent to one another, may be linked together to form a ring structure.

According to a still further aspect of the present invention, there is provided an azaaromatic compound having an azafluoranthene skeleton represented by the following general formula (5) or (5'):

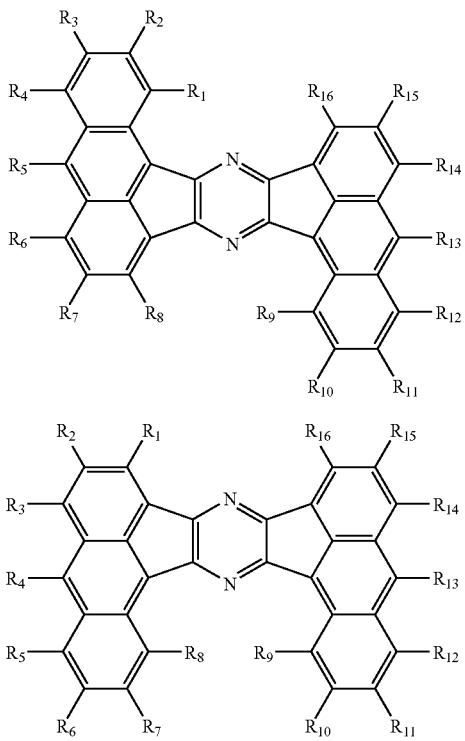

(5)

(5')

wherein $R_1$ to $R_{16}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{16}$ each represent a cyano group, a trifluoromethyl group or a fluorine atom and that those of $R_1$ to $R_{16}$, which are adjacent to one another, may be linked together to form a ring structure.

According to a still another aspect of the present invention, there is provided an azaaromatic compound having an azafluoranthene skeleton represented by the following general formula (6):

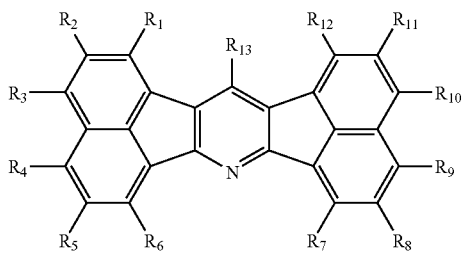

(6)

wherein $R_1$ to $R_{13}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{13}$ each represent a cyano group, a trifluoromethyl group or a fluorine atom and that those of $R_1$ to $R_{13}$, which are adjacent to one another, may be linked together to form a ring structure.

According to a still further aspect of the present invention, there is provided an azaaromatic compound having an azafluoranthene skeleton represented by the following general formula (7):

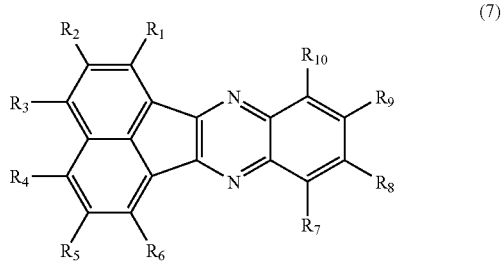

(7)

wherein $R_1$ to $R_{10}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{10}$ each represent a cyano group, a trifluoromethyl group or a fluorine atom and that those of $R_1$ to $R_{10}$, which are adjacent to one another, may be linked together to form a ring structure.

According to a still further aspect of the present invention, there is provided an azaaromatic compound having an azafluoranthene skeleton represented by the following general formula (8):

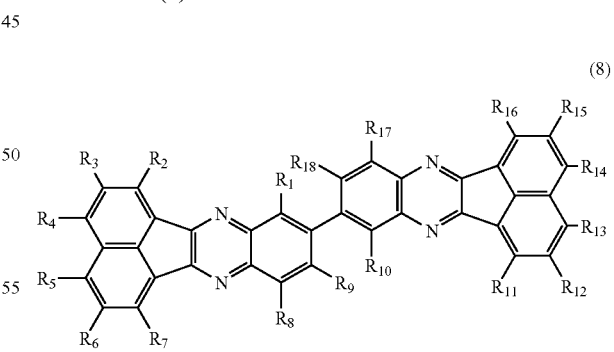

(8)

wherein $R_1$ to $R_{18}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{18}$ each represent a cyano group, a trifluoromethyl group or a fluorine atom and that those of $R_1$ to $R_{18}$ which are adjacent to one another, may be linked together to form a ring structure.

According to a further aspect of the present invention, there is provided an azaaromatic compound having an azafluoranthene skeleton represented by the following general formula (9):

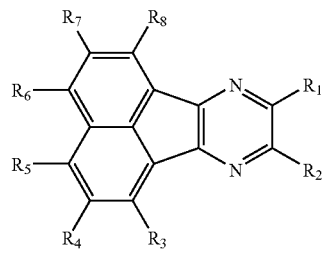

wherein $R_1$ to $R_8$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_8$ each represent a cyano group, a trifluoromethyl group or a fluorine atom and that those of $R_1$ to $R_8$ which are adjacent to one another, may be linked together to form a ring structure.

According to a further aspect of the present invention, there is provided an azaaromatic compound having an azafluoranthene skeleton represented by the following general formula (10):

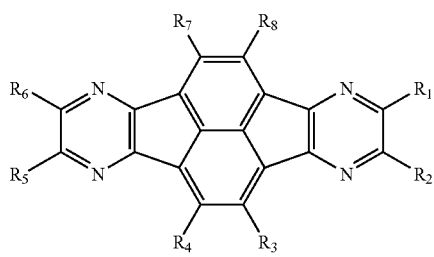

wherein $R_1$ to $R_8$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_8$ each represent a cyano group, a trifluoromethyl group or a fluorine atom and that those of $R_1$ to $R_8$, which are adjacent to one another, may be linked together to form a ring structure.

According to a further aspect of the present invention, there is provided an azaaromatic compound having an azafluoranthene skeleton represented by the following general formula (11):

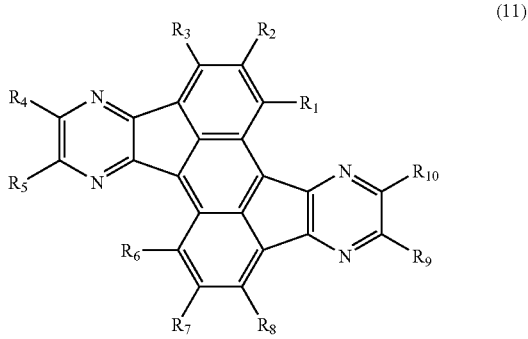

wherein $R_1$ to $R_{10}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{10}$ each represent a cyano group, a trifluoromethyl group or a fluorine atom and that those of $R_1$ to $R_{10}$, which are adjacent to one another, may be linked together to form a ring structure.

The present invention further provides a material for organic EL devices, a hole injecting or hole transporting material for organic EL devices and an electron injecting or electron transporting material for organic EL devices comprising the foregoing azaaromatic compound having the azafluoranthene skeleton according to the present invention.

The present invention further relates to an organic EL device which comprises one or a plurality of organic layers which are interposed between a cathode and an anode, wherein at least one of the organic layers comprises the foregoing azaaromatic compound having an azafluoranthene skeleton according to the present invention.

The present invention further provides an equipment comprising the foregoing organic EL device.

BEST MODE FOR CARRYING OUT THE INVENTION (Azaaromatic Compound Having Azafluoranthene Skeleton)

In respect of the azaaromatic compounds each having an azafluoranthene skeleton represented by the foregoing general formulas (1) to (11), the substituted or unsubstituted alkyl group having 1 to 30 carbon atoms included in the definition of $R_1$ to $R_{12}$ appearing in the general formula (1), $R_1$ to $R_{14}$ appearing in the general formula (2), $R_1$ to $R_{12}$ appearing in the general formula (3), $R_1$ to $R_2$ appearing in the general formula (4), $R_1$ to $R_{16}$ appearing in the general formula (5), $R_1$ to $R_{13}$ appearing in the general formula (6), $R_1$ to $R_{10}$ appearing in the general formula (7), $R_1$ to $R_{18}$ appearing in the general formula (8), $R_1$ to $R_8$ appearing in the general formula (9), $R_1$ to $R_8$ appearing in the general formula (10), and $R_1$ to $R_{10}$ appearing in the general formula (11), may be a linear or branched one. In this respect, the substituent thereof includes hydroxyl, amino, cyano and nitro groups; and halogen atoms. The foregoing alkyl group may have one or a plurality of the foregoing substituents. Specific examples of the alkyl groups are methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl groups; cyclic alkyl groups such as cyclohexyl and cyclopentyl groups; substituted or unsubstituted halogenated alkyl groups having 1 to 30 carbon atoms such as trifluoromethyl, pentafluoroethyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, and 1,2,3-triiodopropyl groups; aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, and 1,2,3-trinitropropyl groups.

Among them, preferably used herein are substituted or unsubstituted alkyl groups having 1 to 10 carbon atoms such as methyl, trifluoromethyl, isopropyl, t-butyl, ethyl, propyl, pentafluoroethyl, and cyanomethyl groups.

In respect of the foregoing azaaromatic compounds each having an azafluoranthene skeleton represented by the foregoing general formulas (1) to (11), the substituted or unsubstituted aryl group having 6 to 40 atoms forming a ring included in the definition of $R_1$ to $R_{12}$ appearing in the general formula (1), $R_1$ to $R_{14}$ appearing in the general formula (2), $R_1$ to $R_{12}$ appearing in the general formula (3), $R_1$ to $R_{12}$ appearing in the general formula (4), $R_1$ to $R_{16}$ appearing in the general formula (5), $R_1$ to $R_{13}$ appearing in the general formula (6), $R_1$ to $R_{10}$ appearing in the general formula (7), $R_1$ to $R_{18}$ appearing in the general formula (8), $R_1$ to $R_8$ appearing in the general formula (9), $R_1$ to $R_8$ appearing in the general formula (10), and $R_1$ to $R_{10}$ appearing in the general formula (11), may be a monocyclic or polycyclic one. Moreover, the substituent thereof includes alkyl groups having 1 to 20 carbon atoms, alkoxy groups having 1 to 20 carbon atoms, and hydroxyl, amino, cyano and nitro groups, and halogen atoms. The foregoing aryl group may have one or a plurality of the foregoing substituents. Specific examples of the aryl groups are phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4''-t-butyl-p-terphenyl-4-yl, fluoranthenyl, and fluorenyl groups.

Among these aryl groups, preferably used herein are substituted or unsubstituted aryl groups having 6 to 20 ring atoms and examples thereof include phenyl, naphthyl, biphenylyl, anthranyl, phenanthryl, pyrenyl, chrysenyl, fluoranthenyl and fluorenyl groups. These groups may be substituted with the substituents specified above.

In respect of the foregoing azaaromatic compounds each having an aza fluoranthene skeleton represented by the foregoing general formulas (1) to (11), the groups other than the foregoing included in the definition of $R_1$ to $R_{12}$ appearing in the general formula (1), $R_1$ to $R_{14}$ appearing in the general formula (2), $R_1$ to $R_{12}$ appearing in the general formula (3), $R_1$ to $R_{12}$ appearing in the general formula (4), $R_1$ to $R_{16}$ appearing in the general formula (5), $R_1$ to $R_{13}$ appearing in the general formula (6), $R_1$ to $R_{10}$ appearing in the general formula (7), $R_1$ to $R_{18}$ appearing in the general formula (8), $R_1$ to $R_8$ appearing in the general formula (9), $R_1$ to $R_8$ appearing in the general formula (10), and $R_1$ to $R_{10}$ appearing in the general formula (11), may be, for instance, those listed below:

The substituted or unsubstituted alkoxy group having 1 to 30 carbon atoms is one represented by the following general formula: —OY, wherein Y and the substituents of the alkoxy group include those listed above in connection with the foregoing alkyl group;

The trialkylsilyl group (the alkyl group is one having 1 to 20 carbon atoms and it may have a substituent) is a group represented by the following general formula: —SiY$_3$, wherein Y and the substituents of the alkoxy group include those listed above in connection with the foregoing alkyl group;

The substituted or unsubstituted aryloxy group having 6 to 40 atoms forming a ring, is one represented by the following general formula: —OY', wherein Y and the substituents of the aryloxy group include those listed above in connection with the foregoing aryl group;

The halogen atom includes fluorine, chlorine, bromine and iodine atoms; and

Examples of other groups include cyano groups.

Among these groups, preferably used herein are fluorine atom, cyano groups and the like.

In this connection, the substituents, which are adjacent to one another and selected from those represented by $R_1$ to $R_{12}$ appearing in the general formula (1), $R_1$ to $R_{14}$ appearing in the general formula (2), $R_1$ to $R_{12}$ appearing in the general formula (3), $R_1$ to $R_{12}$ appearing in the general formula (4), $R_1$ to $R_{16}$ appearing in the general formula (5), $R_1$ to $R_{13}$ appearing in the general formula (6), $R_1$ to $R_{10}$ appearing in the general formula (7), $R_1$ to $R_{18}$ appearing in the general formula (8), $R_1$ to $R_8$ appearing in the general formula (9), $R_1$ to $R_8$ appearing in the general formula (10), and $R_1$ to $R_{10}$ appearing in the general formula (11), may preferably be linked together to form an aromatic ring structure, more preferably a 5-membered aromatic ring or a 6-membered aromatic ring and particularly preferably a 6-membered aromatic ring.

Specific examples of the foregoing azaaromatic compounds each having an azafluoranthene skeleton represented by the general formulas (1) to (11) will be given below:

(1)

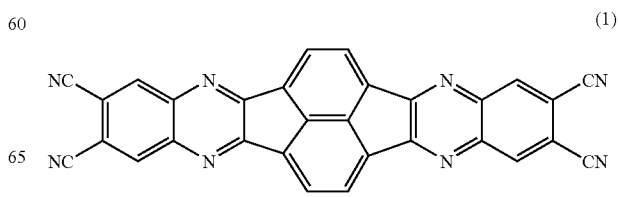

-continued
(2)
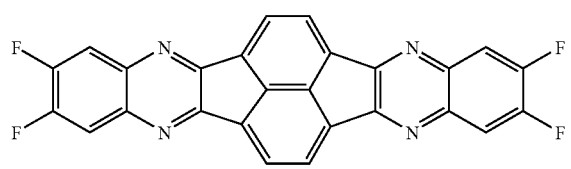
(3)
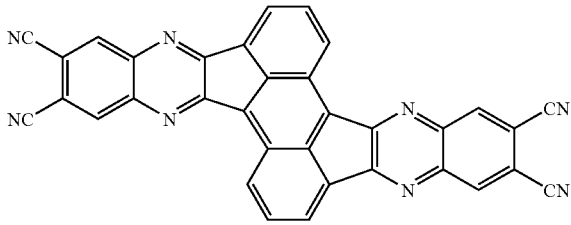
(4)
(5)
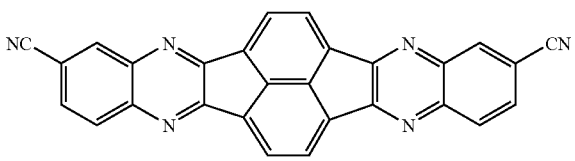
(6)
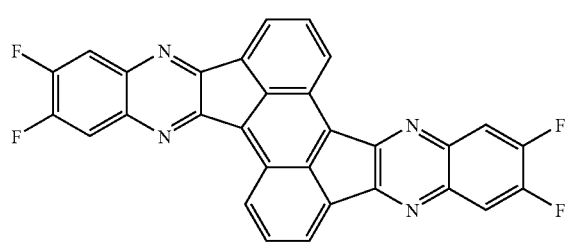
(7)
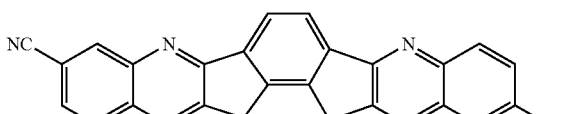
(8)
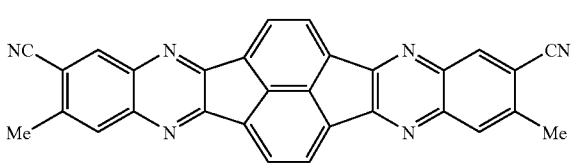
-continued
(9)
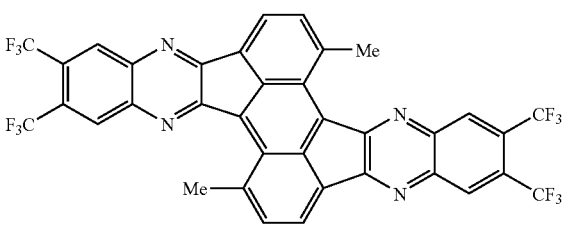
(10)
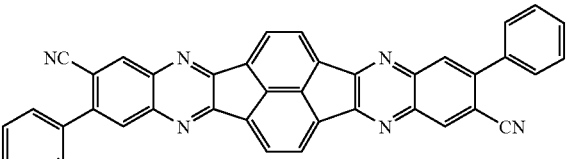
(11)
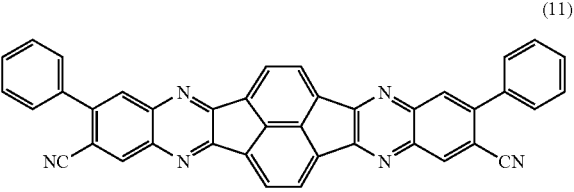
(12)
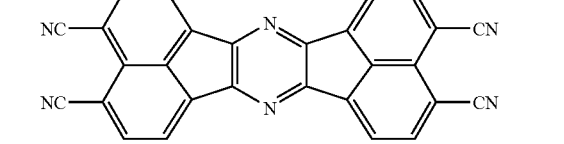
(13)
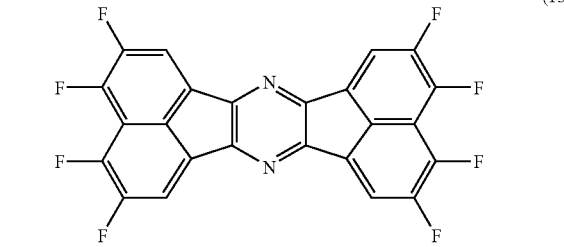
(14)
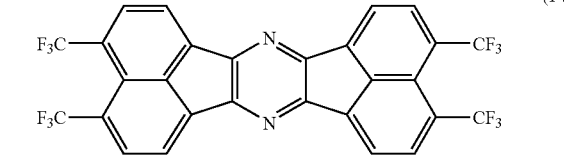
(15)
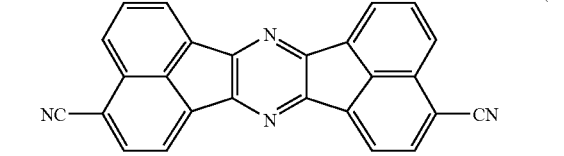
(16)
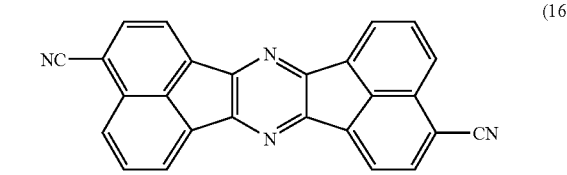

-continued
(17)
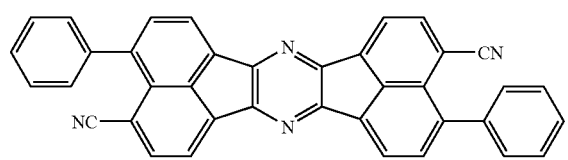
(18)
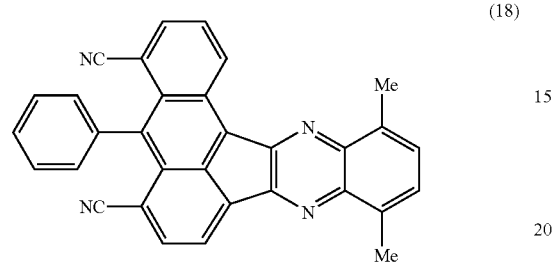
(19)
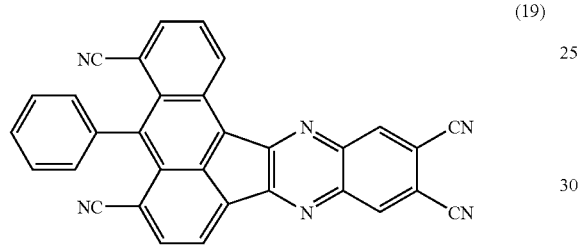
(20)
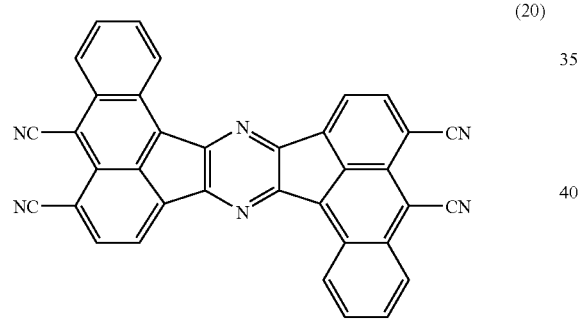
(21)
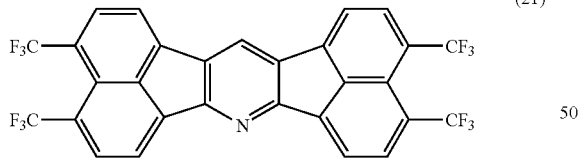
(22)
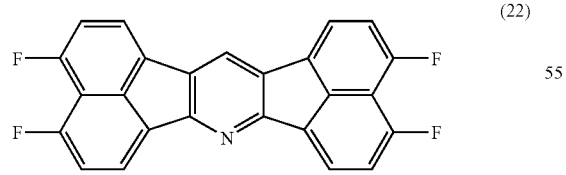
(23)
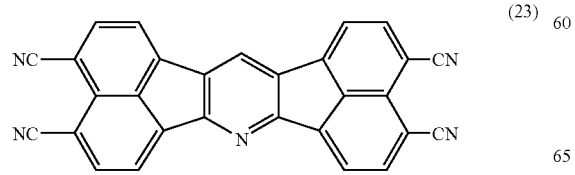
-continued
(24)
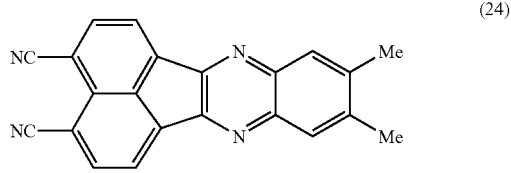
(25)
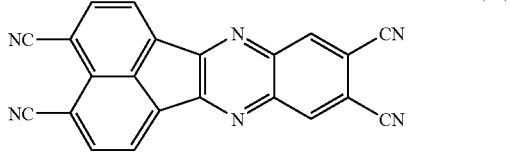
(26)
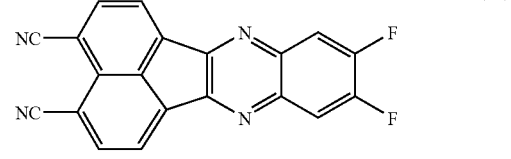
(27)
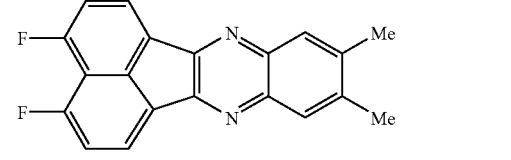
(28)
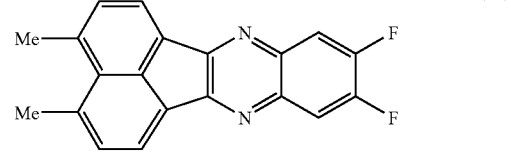
(29)
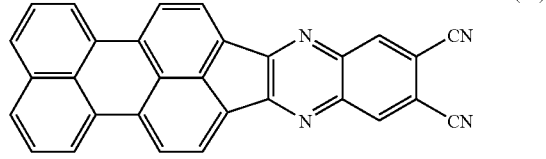
(30)
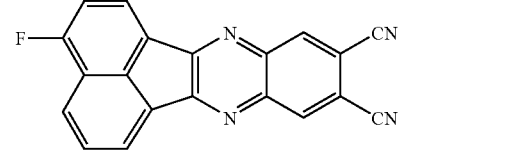
(31)
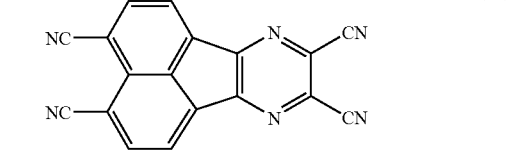
(32)
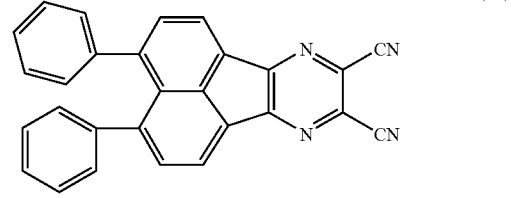

-continued
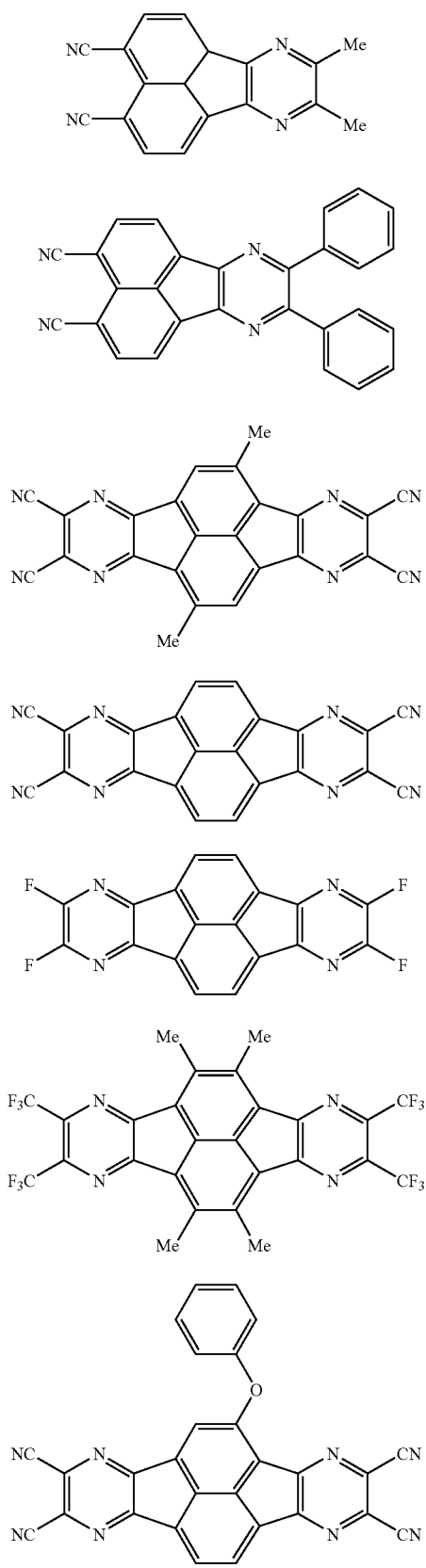
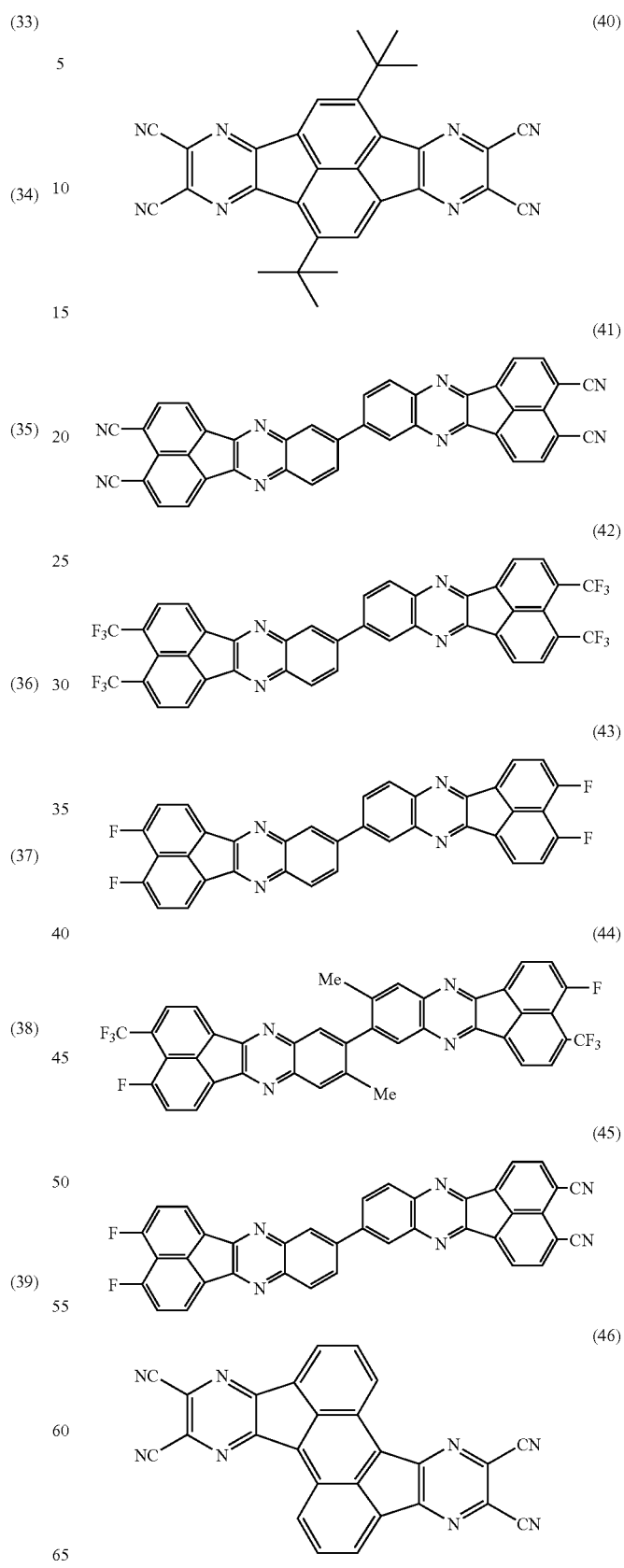

-continued
(47)
(48)
(49)
(50)
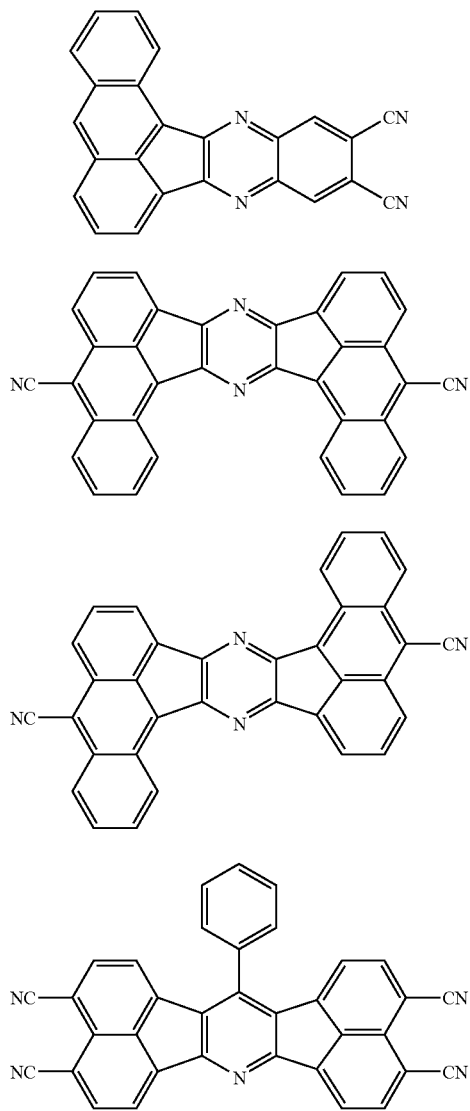
(Method for Synthesizing an Azaaromatic Compound Having an Azafluoranthene Skeleton)
The following are the schemes for synthesizing the compounds represented by the general formula (1) to (11):
General Formula (1):
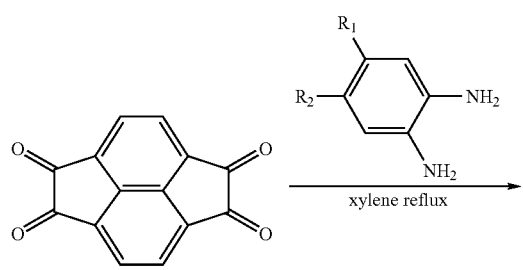
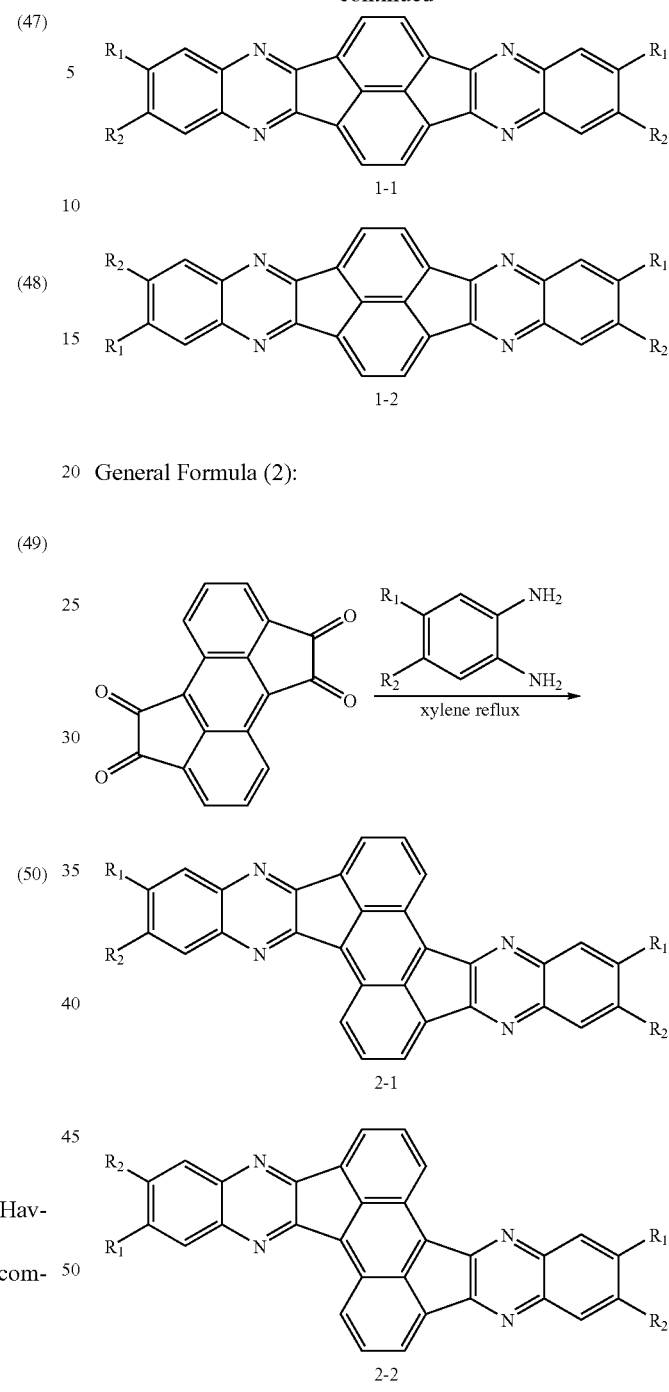
1-1
1-2
General Formula (2):
2-1
2-2
General Formula (3):
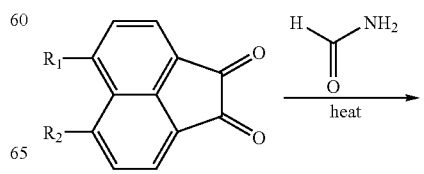

-continued
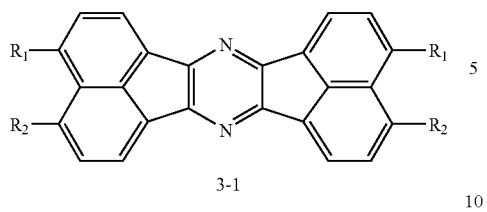
3-1
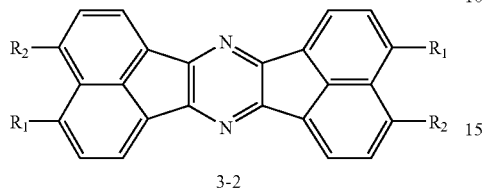
3-2
General Formula (4):
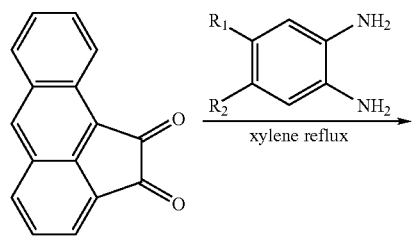
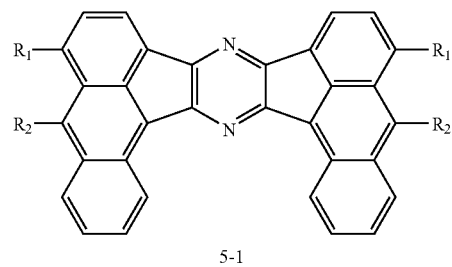
5-1
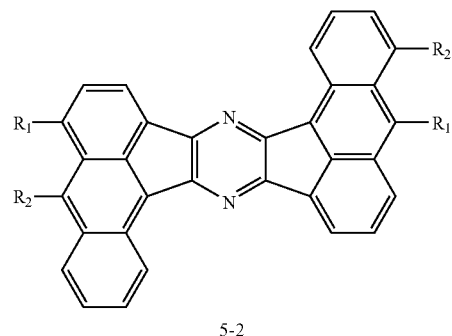
5-2
General Formula (6):
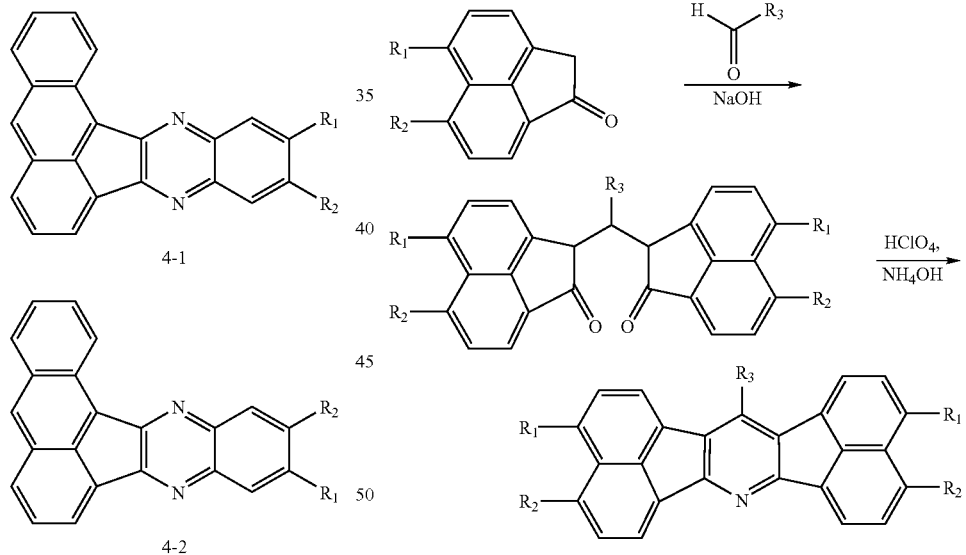
4-1
4-2
General Formula (5):
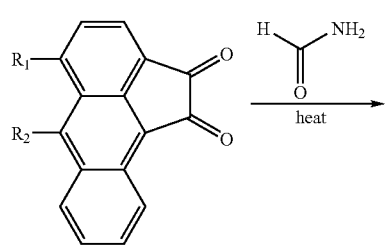
General Formula (7):
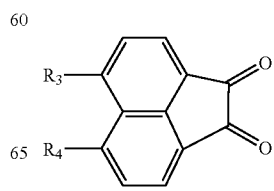
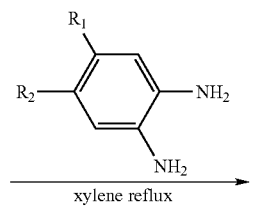

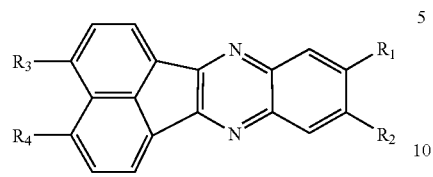
7-1
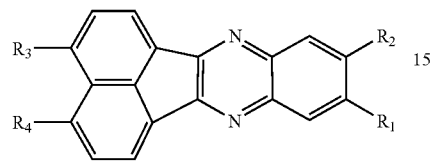
7-2
General Formula (8):
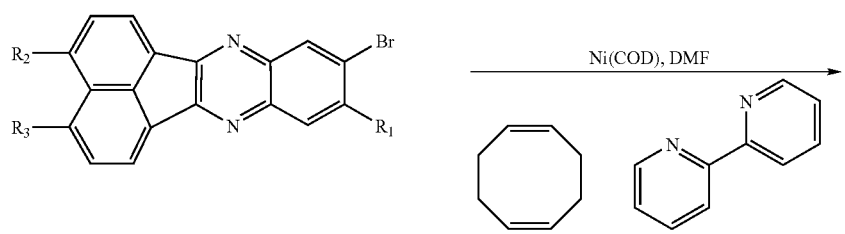
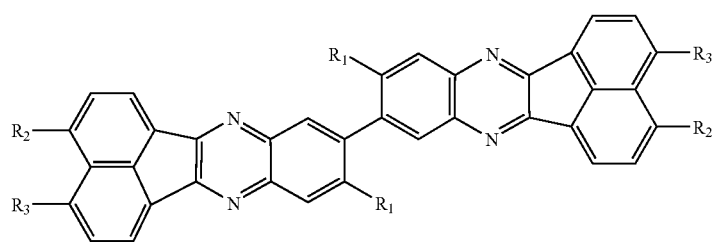
8
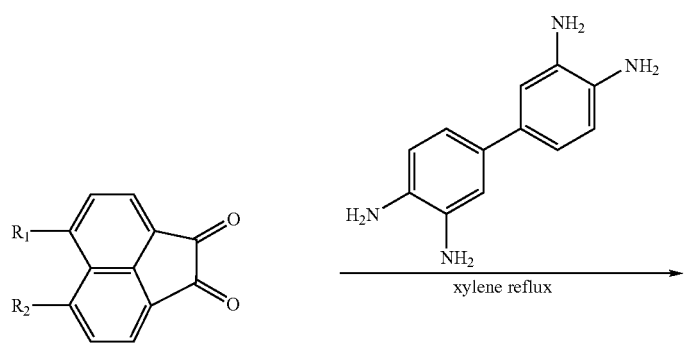

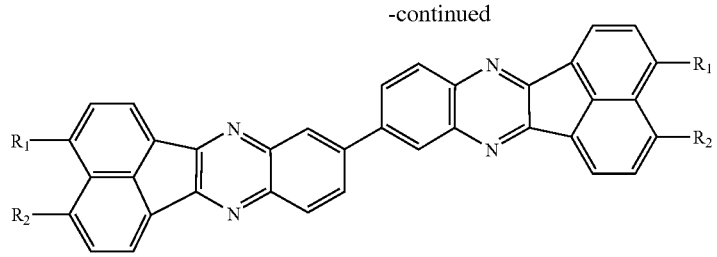
8-1
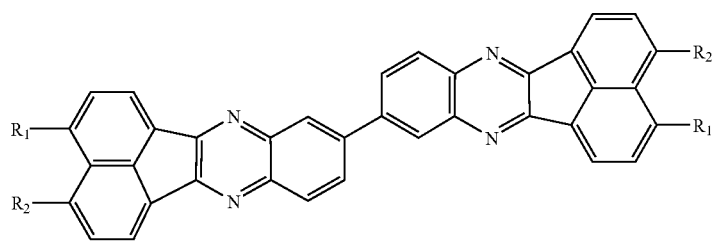
8-2
General Formula (9):
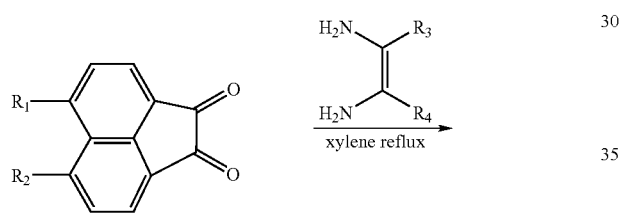
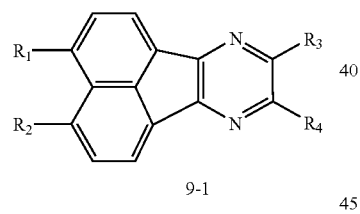
9-1
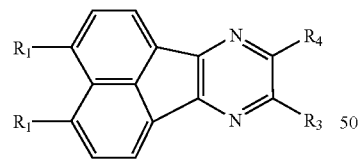
9-2
General Formula (10):
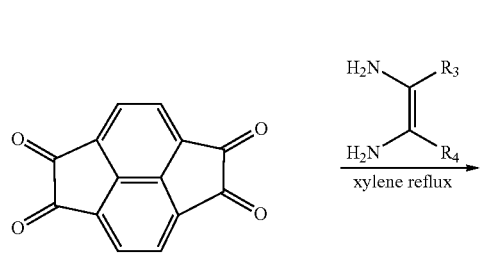
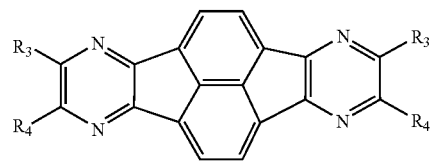
10-1
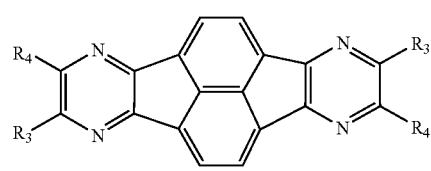
10-2
General Formula (11):
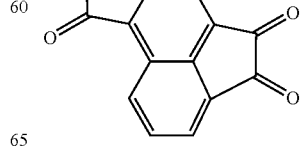 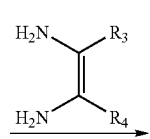

-continued

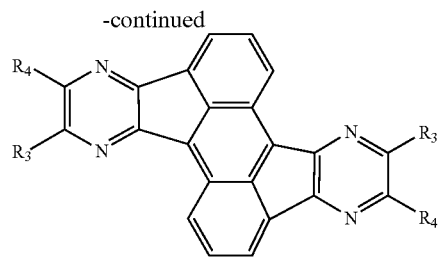

(Organic EL Device)

The organic EL device according to the present invention is an organic electroluminescence device which comprises one or a plurality of organic layers which are interposed between a cathode and an anode, wherein at least one of the organic layers comprises the azaaromatic compound having the azafluoranthene skeleton of the present invention.

The following are representative constructions of the organic EL device according to the present invention, but the present invention is not restricted to these specific constructions:

(1) Anode/emitting layer/cathode;
(2) Anode/hole injection layer/emitting layer/cathode;
(3) Anode/emitting layer/electron injection layer/cathode;
(4) Anode/hole injection layer/emitting layer/electron injection layer/cathode;
(5) Anode/organic semiconductor layer/emitting layer/cathode;
(6) Anode/organic semiconductor layer/electron blocking layer/emitting layer/cathode;
(7) Anode/organic semiconductor layer/emitting layer/adhesion improving layer/cathode;
(8) Anode/hole injection layer/hole transporting layer/emitting layer/electron injection layer/cathode;
(9) Anode/insulating layer/emitting layer/insulating layer/cathode;
(10) Anode/inorganic semiconductor layer/insulating layer/emitting layer/insulating layer/cathode;
(11) Anode/organic semiconductor layer/insulating layer/emitting layer/insulating layer/cathode;
(12) Anode/insulating layer/hole injection layer/hole transporting layer/emitting layer/insulating layer/cathode;
(13) Anode/insulating layer/hole injection layer/hole transporting layer/emitting layer/electron injection layer/cathode.

Preferably used herein are those having the construction (8), among them.

The azaaromatic compound having the azafluoranthene skeleton of the present invention may be used in any organic layers constituting the foregoing organic EL device. For instance, the azaaromatic compound may be incorporated into the hole injection layer or the hole transporting layer as a hole injecting material or a hole transporting material for organic EL devices, using a hole injection or hole transporting property of the compound. Alternatively, the azaaromatic compound may be incorporated into the electron injection layer or the electron transporting layer as an electron injecting material or an electron transporting material for organic EL devices, using an electron injection or the electron transportation property of the compound. If using an azaaromatic compound to which 4 cyano groups are linked, as the azaaromatic compound having the azafluoranthene skeleton, in the foregoing organic EL device, the driving voltage of the resulting device can substantially be reduced, through the improvement of the charge injecting and charge transporting ability thereof. This is preferable in terms of the power efficiency of the device.

(Light-Transmissive Substrate)

If the organic EL device is a back face emitting type or bottom emission type one, which can emit light through the substrate, the EL device of the present invention is formed on a light-transmissive substrate. The light-transmissive substrate herein used is preferably a substrate supporting the organic EL device and having a smooth surface and having 50% or more of the light transmittance for the visible range of 400 to 700 nm. Specific examples of such substrates include a glass plate and a polymer plate.

Examples of the above glass plate include, in particular, soda-lime glass, barium/strontium-containing glass, lead glass, aluminosolicate glass, borosilicate glass, barium-borosilicate glass, and quartz. On the other hand, examples of the above polymer plate include polycarbonate, acrylic resins, polyethylene terephthalate, polyether sulfide and polysulfone. Moreover, the substrate may be a TFT substrate on which a TFT for driving is formed.

Alternatively, if the organic EL device is an upper face emitting type or top emission type one, which can emit light through the top of the device, it is necessary to form a light reflection layer of a proper metal such as aluminum on the foregoing substrate.

(Anode)

The anode of the organic EL device according to the present invention serves to inject holes into the hole transporting layer or the emitting layer and it would be effective that the anode has 4.5 eV or more of the work function. Specific examples of the anode materials used in the present invention include indium tin oxide alloy (ITO), tin oxide (NESA), indium zinc oxide (IZO), gold, silver, platinum, and copper.

The anode may be produced by forming a thin film of the foregoing electrode material according to any method such as the vacuum evaporation method or the sputtering method.

In case of a back face emitting type or bottom emission type organic EL device, the anode preferably has over 10% of the transmittance with respect to the emitted light through the anode. In addition, the anode preferably has not more than several hundreds of ohms ($\Omega$)/□ of the sheet resistance. The film thickness of the anode may vary depending on the material selected, but the anode in general has 10 nm to 1 μm and preferably 10 to 200 nm of the thickness.

(Emitting Layer)

The emitting layer of the organic EL device is one having the following functions (1) to (3) in combination:
(1) Injection Function: This function permits the injection of holes through the anode or the hole injection layer and the injection of electrons through the cathode or the electron injection layer upon the application of an electric field to the EL device;
(2) Transporting Function: This function permits the transfer of the injected charges (electrons and holes) by the action of the electric field applied to the device;
(3) Emitting Function: This function permits the provision of a field for the recombination of electrons with holes to thus induce the emission of light.

However, although the emitting layer may have a difference between the hole injectability and the electron injectability, or a difference between the transport capacities represented by the hole mobility and electron mobility respectively, it is preferred to move either one of the hole and electron.

This emitting layer can be prepared by any known method such as the vacuum evaporation method, the spin coating method, and the LB method. The emitting layer is particularly preferably a molecular deposit film. In this respect, the term "molecular deposit film" used herein means a thin film formed by the deposition of a raw compound in a gaseous state; or a film formed through the solidification of a raw compound in a solution or liquid state and thus can in general be distinguished from the thin film (molecular accumulation film) formed using the LB method, on the basis of the differences in the aggregation structure and in the higher-order structure as well as the difference in the functions due to the foregoing structural differences.

In addition, the emitting layer may likewise be prepared by a method comprising preparing a solution of a binder such as a resin and a raw compound by dissolving them in a solvent and then forming a thin film using the resulting solution according to the spin coating method, as disclosed in J.P. KOKAI Sho 57-51781.

In the present invention, the emitting materials or the host materials usable in the emitting layer include, for instance, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminoanthracene, diaminocarbazole, pyran, thiopyran, polymethine, merocyanine, imidazole-chelated oxinoid compounds, quinacridone, rubrene, stilbene, derivatives having the foregoing skeletons and fluorescent dyes, but the materials is not restricted to these specific examples.

Moreover, the emitting layer of the organic EL device according to the present invention can likewise be applied to the EL device comprising a phosphorescent emitting dopant. In this case, specific examples of materials contained in the emitting layer include compounds having substituted or unsubstituted indole skeletons, substituted or unsubstituted carbazole skeletons, substituted or unsubstituted azacarbazole skeletons and arylsilane skeletons, and those comprising organometal complexes. In addition, it is also possible to use the compounds listed above in connection with the preferred examples of the foregoing hole transporting and electron transporting materials. It is preferred that the T1 (the energy level of the lowest triplet excited state) of the foregoing host material is higher than the T1 level of the phosphorescent emitting dopant serving as a guest material.

Although the phosphorescent emitting dopant may be any one as long as it is a material capable of emitting phosphorescence within the temperature range in which the device would certainly operate, Ir, Pt, Os, Pd and Au-containing complexes are preferably. Among them, particularly preferably used herein are Ir and Pt-containing complexes. The following are specific examples thereof:

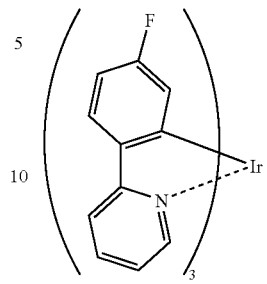

(K-1)

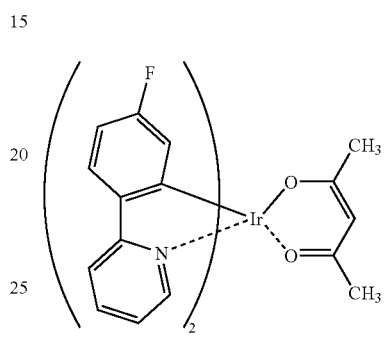

(K-2)

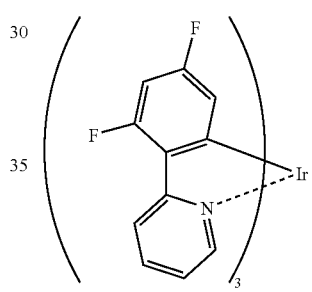

(K-3)

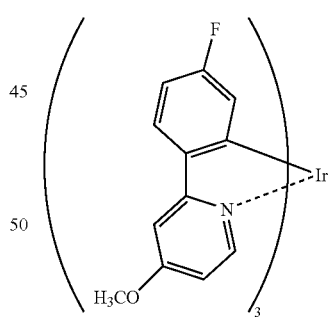

(K-4)

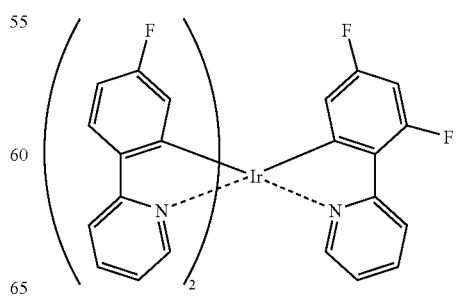

(K-5)

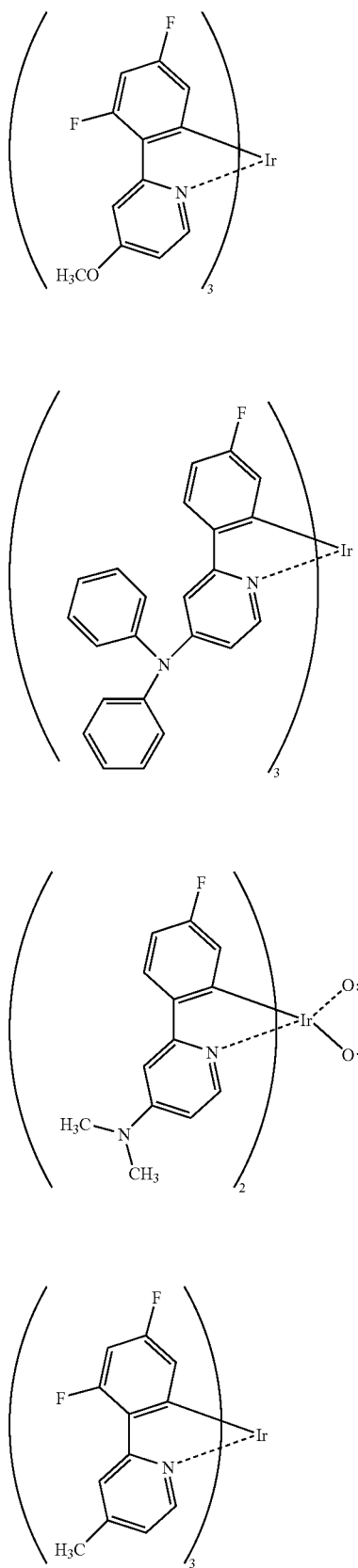
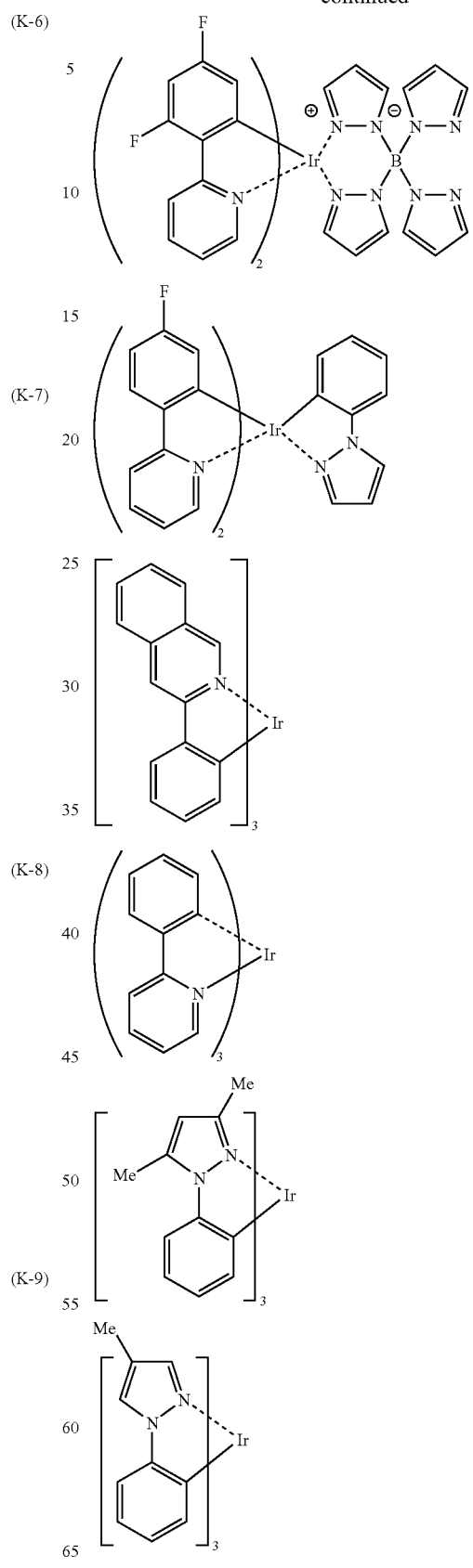

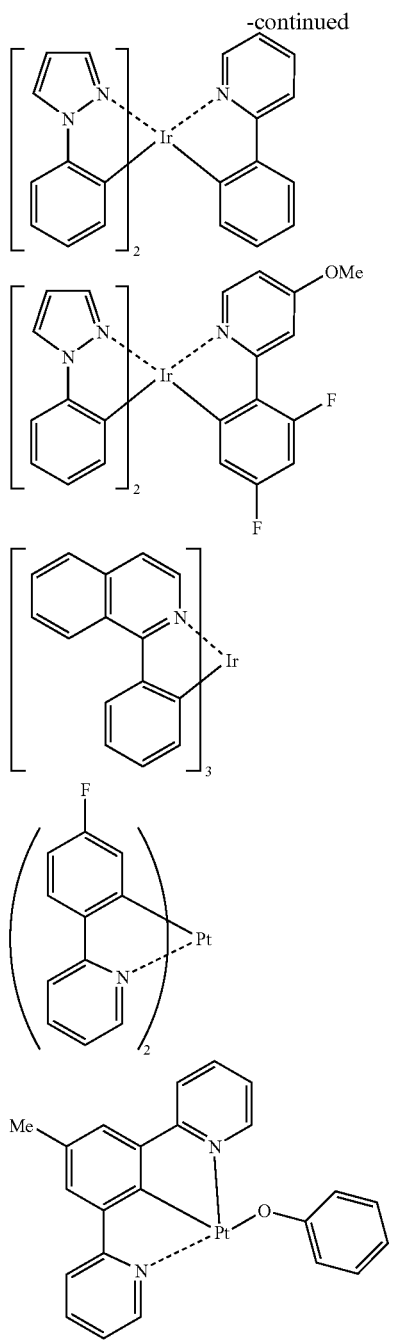

(Hole Injecting and Transporting Layer (Hole Transporting Zone))

The hole injecting and transporting layer is a layer for helping the injection of holes into the emitting layer and for transporting the holes to the emitting zone, and has a high hole mobility and in general a low ionization energy which is 5.5 eV or less. A material for such a hole injecting and transporting layer is preferably a material which permits the transportation of holes to the emitting layer at a lower electric field strength and further preferably, for instance, a material which has at least $10^{-4}$ cm$^2$/V of the hole mobility when applying an electric field of $10^4$ to $10^6$ V/cm to the layer.

When the compound of the present invention is used in the hole transporting zone, the hole injecting and transporting layer may be formed from the compound of the present invention alone or in combination with another material. The material used for forming the hole injecting and transporting layer in combination with the compound of the present invention is not restricted to any specific one as long as it has the above preferred characteristic properties and thus can be selected from the group consisting of the conventional hole transport materials currently used in the photoconductive materials and known materials for a hole injecting layer of organic EL devices.

Specific examples of such materials for the hole injecting and transporting layer of the present invention are triazole derivatives (see, for instance, U.S. Pat. No. 3,112,197); oxadiazole derivatives (see, for instance, U.S. Pat. No. 3,189,447); imidazole derivatives (Japanese Examined Patent Publication (hereunder referred to as "J.P. KOKOKU") Sho 37-16096); polyarylalkane derivatives (see, for instance, U.S. Pat. Nos. 3,615,402, 3,820,989 and 3,542,544; J.P. KOKOKU Nos. Sho 45-555 and Sho 51-10983; and J.P. KOKAI Nos. Sho 51-93224, Sho 55-17105, Sho 56-4148, Sho 55-108667, Sho 55-156953 and Sho 56-36656); pyrazoline derivatives and pyrazolone derivatives (see, for instance, U.S. Pat. Nos. 3,180,729 and 4,278,746; and J.P. KOKAI Nos. Sho 55-88064, Sho 55-88065, Sho 49-105537, Sho 55-51086, Sho 56-80051, Sho 56-88141, Sho 57-45545, Sho 54-112637 and Sho 55-74546); phenylenediamine derivatives (see, for instance, U.S. Pat. No. 3,615,404; and J.P. KOKOKU Nos. Sho 51-10105, Sho 46-3712 and Sho 47-25336; and J.P. KOKAI Nos. Sho 54-53435, Sho 54-110536 and 54-119925); arylamine derivatives (see, for instance, U.S. Pat. Nos. 3,567,450, 3,180,703, 3,240,597, 3,658,520, 4,232,103, 4,175,961 and 4,012,376; J.P. KOKOKU Nos. Sho 49-35702 and Sho 39-27577; J.P. KOKAI Nos. Sho 55-144250, Sho 56-119132 and Sho 56-22437; and German Patent No. 1,110,518); amino-substituted chalcone derivatives (see, for instance, U.S. Pat. No. 3,526,501); oxazole derivatives (such as those disclosed in, for instance, U.S. Pat. No. 3,257,203); styrylanthracene derivatives (see, for instance, J.P. KOKAI No. Sho 56-46234); fluorenone derivatives (see, for instance, J.P. KOKAI No. Sho 54-110837); hydrazine derivatives (see, for instance, U.S. Pat. No. 3,717,462; and J.P. KOKAI Nos. Sho 54-59143, Sho 55-52063, Sho 55-52064, Sho 55-46760, Sho 55-85495, Sho 57-11350, Sho 57-148749, and Hei 2-311591); stilbene derivatives (see, for instance, J.P. KOKAI Nos. Sho 61-210363, Sho 61-228451, Sho 61-14642, Sho 61-72255, Sho 62-47646, Sho 62-36674, Sho 62-10652, Sho 62-30255, Sho 60-93455, Sho 60-94462, Sho 60-174749 and Sho 60-175052); silazane derivatives (see, for instance, U.S. Pat. No. 4,950,950); polysilane type (see J.P. KOKAI No. Hei 2-204996); and aniline copolymers (see J.P. KOKAI No. Hei 2-282263); and conducting high molecular weight oligomers disclosed in J.P. KOKAI Hei 1-211399 (in particular, thiophene oligomers).

Although the materials listed above can be used for the hole injecting and transporting layer, porphyrin compounds (such as those disclosed in, for instance, J.P. KOKAI No. Sho 63-295695); aromatic tertiary amine compounds and styrylamine compounds (see, for instance, U.S. Pat. No. 4,127,412; and J.P. KOKAI Nos. Sho 53-27033, Sho 54-58445, Sho 54-149634, Sho 54-64299, Sho 55-79450, Sho 55-144250, Sho 56-119132, Sho 61-295558, Sho 61-98353 and Sho 63-295695), in particular, aromatic tertiary amine compounds are preferable.

In addition, materials for the hole injecting and transporting layer includes compounds each having two fused aromatic rings in the molecule as disclosed in U.S. Pat. No. 5,061,569 such as 4,4'-bis(N-(1-naphthyl)-N-phenylamino)

biphenyl (hereunder abbreviated as "NPD") and those disclosed in J.P. KOKAI Hei 4-308688 such as 4,4',4"-tris(N-(3-methylphenyl)-N-phenylamino)triphenylamine (hereunder abbreviated as "MTDATA") in which three triphenylamine units are connected in the form of a star burst-like shape.

In addition to the aromatic dimethylidyne type compounds already described above as the materials for the emitting layer, inorganic compounds such as p-type Si and p-type SiC can likewise be used as materials for the hole injecting layer.

The hole injecting and transporting layer can be prepared by forming the compound of the present invention into a thin film according to any known methods such as the vacuum evaporation method, the spin coating method, the casting method, and the LB method. The thickness of the hole injecting and transporting layer is not restricted to any particular level, but it in general ranges from 5 nm to 5 μm. This hole injecting and transporting layer may comprise a single layer containing one or at least two kinds of the foregoing materials, or it may be a laminate with a hole injecting and transporting layer comprising a compound different from that used for forming the foregoing hole injecting and transporting layer as long as the hole transporting zone contains the foregoing hole injecting and transporting material.

In addition, it is also possible to form an organic semiconductor layer as a layer for helping the hole injection or electron injection into the emitting layer and the organic semiconductor layer preferably has $10^{-10}$ S/cm or more of the conductivity. Materials for such an organic semiconductor layer include conductive oligomers such as thiophene-containing oligomers and arylamine-containing oligomers as those disclosed in J.P. KOKAI Hei 8-193191; and conducting dendorimers such as arylamine-containing dendorimers.

(Electron Injecting and Transporting Layer (Electron Transporting Zone))

The electron injecting and transporting layer is a layer for helping the injection of electrons into the emitting layer and for transporting the holes to the emitting zone, and has a high electron mobility, while an adhesion improving layer is one of the electron injecting layers, which consists of a material excellent in the adhesion to the cathode. The electron injecting and transporting layer may be formed from the compound of the present invention alone or in combination with another material.

The material used for forming the electron injecting and transporting layer in combination with the compound of the present invention is not restricted to any specific one as long as it has the above preferred characteristic properties and thus can be selected from known ones used for the electron injecting and transporting layer of the organic EL device. Moreover, it is also possible to use a hole blocking layer. Particularly, in a phosphorescent device, in addition to the foregoing, compounds each having a nitrogen atom-containing 5- or 6-membered ring or a fused ring thereof in its skeleton and compounds each having a π electron deficient type skeleton are preferable. Specific examples thereof include compounds having carbazole, indole, azacarbazole, pyridine, pyrazine, pyrimidine, triazine, triazole, pyrrole, imidazole, and benzimidazole skeletons.

Other materials suitably used for the electron injecting and transporting layer in addition to the foregoing compounds include 8-hydroxyquinoline and metal complexes of the derivatives thereof. Specific examples of such 8-hydroxyquinoline and metal complexes of the derivatives thereof include metal chelated oxinoid compounds including chelates of oxine (in general, 8-quinolinol or 8-hydroxyquinoline). For instance, tris(8-quinolinol)aluminum (Alq) can be used as an electron injecting material.

On the other hand, examples of the oxadiazole derivatives include the electron transport compounds represented by the following general formula:

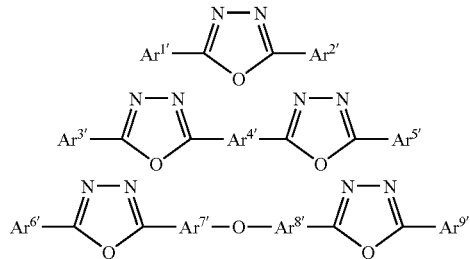

wherein $Ar^{1'}$, $Ar^{2'}$, $Ar^{3'}$, $Ar^{5'}$, $Ar^{6'}$ and $Ar^{9'}$ may be the same or different and each of them represents a substituted or unsubstituted aryl group. In addition, $Ar^{4'}$, $Ar^{7'}$ and $Ar^{8'}$ may be the same or different and each of them represents a substituted or unsubstituted arylene group.

In this connection, examples of such aryl groups are phenyl, biphenyl, anthranyl, perylenyl, and pyrenyl groups. Moreover, examples of the foregoing arylene groups are phenylene, naphthylene, biphenylene, anthranylene, perylenylene, and pyrenylene groups. Moreover, examples of substituents of the foregoing aryl and arylene groups are alkyl groups each having 1 to 10 carbon atoms, alkoxy each having 1 to 10 carbon atoms and cyano groups. As such electron transport compounds, preferably used herein include those having a thin film-forming ability. Specific examples of the foregoing electron transport compounds include those listed below:

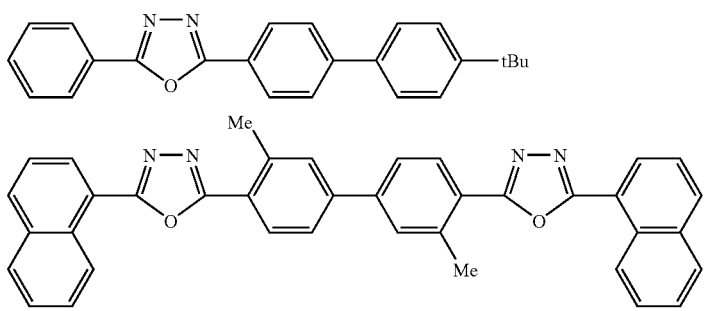

-continued

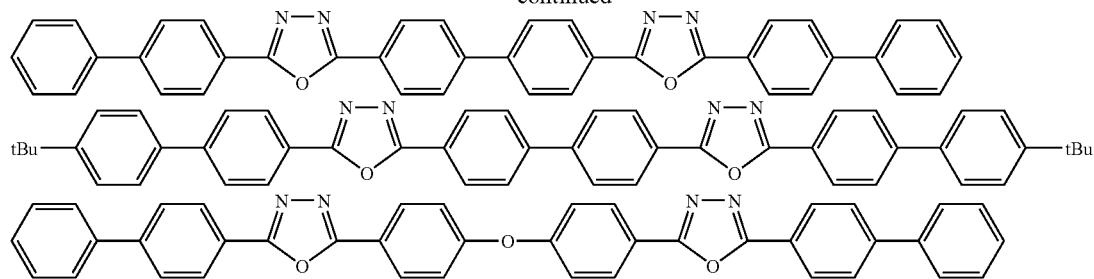

In the organic EL device of the present invention, it is preferred to use, as materials for constituting the electron injecting and transporting layer, inorganic materials such as insulating materials or semiconductor materials. If the electron injecting and transporting layer is composed of a insulating material or a semiconductor material, this would permit the effective prevention of any leakage of the electric current to thus improve the electron injecting ability. Such insulating materials preferably used herein are at least one metal compound selected from the group consisting of alkali metal chalcogenides, alkaline earth metal chalcogenides, halides of alkali metals, and halides of alkaline earth metals. It is preferred that the electron injecting and transporting layer is constituted by such an alkali metal chalcogenide and the like, since this in turn leads to the further improvement of the electron injecting ability of the layer.

Specifically, preferred examples of alkali metal chalcogenides include $Li_2O$, $K_2O$, $Na_2S$, $Na_2Se$ and $Na_2O$, and preferred examples of alkaline earth metal chalcogenides include CaO, BaO, SrO, BeO, BaS and CaSe. In addition, preferred examples of halides of alkali metals include LiF, NaF, KF, LiCl, KCl and NaCl. Furthermore, preferred examples of alkaline earth metal halides include fluorides such as $CaF_2$, $BaF_2$, $SrF_2$, $MgF_2$ and $BeF_2$, and halides thereof other than fluorides.

In addition, semiconductor materials for constructing the electron transporting layer include oxides, nitrides and oxynitrides containing at least one element selected from the group consisting of Ba, Ca, Sr, Yb, Al, Ga, In, Li, Na, Cd, Mg, Si, Ta, Sb and Zn. The above semiconductor materials may be used alone or in any combination of at least two of them. In this connection, the inorganic compound constituting the electron transporting layer is preferably in the form of a microcrystalline or amorphous insulating thin film. If the electron transporting layer is constituted by the above insulating thin film, a more uniform insulating thin film can be formed and therefore, the defects of picture elements such as the formation of dark spots can substantial be reduced. In this respect, such inorganic compounds include those already listed above such as alkali metal chalcogenides, alkaline earth metal chalcogenides, halides of alkali metals and halides of alkaline earth metals.

In the organic EL device of the present invention, the electron injecting layer and/or the electron transporting layer may comprise a reducing dopant having 2.9 eV or less of the work function. In the present inventions, the reducing dopant means a substance which can increase the electron injection efficiency.

Moreover, it is preferred in the present invention that a reducing dopant is added to the boundary region between the organic thin film layer and the cathode and at least part of the organic layer included in the boundary region is reduced to thus form anions. The reducing dopants are preferable at least one member selected from the group consisting of alkali metals, oxides of alkaline earth metals, alkaline earth metals, rare earth metals, alkali metal oxides, alkali metal halides, oxides of alkaline earth metals, alkaline earth metal halides, rare earth metal oxides or rare earth metal halides, alkali metal complexes, alkaline earth metal complexes and rare earth metal complexes. More specifically, examples of the foregoing reducing dopants preferably used in the invention include at least one alkali metal selected from the group consisting of Na (Work Function: 2.36 eV), K (Work Function: 2.28 eV), Rb (Work Function: 2.16 eV) and Cs (Work Function: 1.95 eV); and at least one alkaline earth metal selected from the group consisting of Ca (Work Function: 2.9 eV), Sr (Work Function: 2.0 to 2.5 eV) and Ba (Work Function: 2.52 eV), with those having 2.9 eV of the work function being particularly preferably. Among them, more preferably used herein as the reducing dopants are at least one alkali metal selected from the group consisting of K, Rb and Cs, further preferably used herein are Rb and Cs, and most preferably used herein is Cs. These alkali metals show a particularly high reducing ability and they would permit the improvement of the luminance of the emitted light and the substantial extension of the lifetime of the resulting organic EL device through the addition thereof to the electron injecting zone even in a relatively small quantity.

Examples of the foregoing alkaline earth metal oxides preferably used herein include BaO, SrO, CaO and mixture thereof: $Ba_xSr_{1-x}O$ ($0 \leq x \leq 1$), BaxCal-xO ($0 \leq x \leq 1$). Examples of alkali metal oxides and fluorides are LiF, $Li_2O$, and NaF. Examples of alkali metal complexes, alkaline earth metal complexes and rare earth metal complexes are not restricted to particular ones as long as each of them comprises at least one metal ion selected from alkali metal, alkaline earth metal, and rare earth metal ions. In addition, examples of ligands include quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivatives thereof, but is not restricted to these specific ones.

In addition, the reducing dopant is preferably formed in a layer or in an island-like shape. When the reducing dopant is used in the form of a layer, the thickness thereof preferably ranges from 0.05 to 8 nm.

The electron injecting and transporting layer comprising the reducing dopant is preferably formed according to a method which comprises the steps of vapor deposition the reducing dopant by the resistance heating evaporation method, while simultaneously evaporating an organic material serving as an emitting or electron injecting material, which can in turn form a boundary region to thus disperse the reducing dopant in the organic material. The dispersion density of the reducing dopant ranges from 100:1 to 1:100 and preferably 5:1 to 1:5 as expressed in terms of the molar ratio. When the reducing dopant is formed into a layer, an emitting or electron injecting material for the organic layer at the boundary is formed into a layer and then the reducing dopant alone is vapor deposition by the resistance heating evaporation method in a thickness preferably ranging from 0.5 nm to 15 nm. When the reducing dopant is formed in an island-like shape, an emitting or electron injecting material for the organic layer at the boundary is formed into a layer and then a reducing dopant alone is vapor deposition onto the same by the resistance heating evaporation method in a thickness preferably ranging from 0.05 nm to 1 nm.

(Cathode)

The cathode of the organic EL device of the present invention serves to supply electrons to the electron injecting layer, electron transporting layer or a emitting layer and examples of materials for the cathode include a metal, an alloy, a metal halide, a metal oxide, an electroconductive compound or a mixture thereof. Specific examples of such cathode materials include alkali metals (such as Li, Na, and K) and fluorides and oxides thereof, alkaline earth metals (such as Mg, and Ca) and fluorides and oxides thereof; gold, silver, lead, aluminum, sodium-potassium alloys or sodium-potassium mixed metals, lithium-aluminum alloys or lithium-aluminum mixed metals, magnesium-silver alloys or magnesium-silver mixed metals, or rare earth metals such as indium and ytterbium. Among these materials, preferably used herein are aluminum, lithium-aluminum alloys or lithium-aluminum mixed metals, and magnesium-silver alloys or magnesium-silver mixed metals. The cathode may have a monolayer structure of the foregoing materials or a laminated structure comprising layers containing the foregoing materials. For instance, laminate structures include aluminum/lithium fluoride and aluminum/lithium oxide are preferable. The thickness of the cathode may arbitrarily be selected depending on the material selected.

This cathode can be prepared by forming such an electrode material into a thin film using the evaporation method, the sputtering method or the like.

In this connection, when the organic EL device is a top face emitting type or top emission type, the cathode preferably has over 10% of the transmittance with respect to the emitted light.

In addition, the cathode preferably has several hundreds of ohms ($\Omega$)/□ or less the sheet resistance. The cathode has usually 10 nm to 1 $\mu$m and preferably 50 to 200 nm of the thickness.

(Insulating Layer)

In the organic EL device, an electric field is applied to an ultrathin film and accordingly, the device is subject to pixel defects due to any leakage and/or short circuit. To prevent said defects, it is preferred that an insulating thin film layer is interposed between the paired electrodes.

Examples of materials used for such an insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. It is also possible to use a mixture of the foregoing materials or a laminate of the foregoing materials.

(Method for the Preparation of Organic EL Device)

The organic EL device can be prepared by forming an anode, an emitting layer, a hole injecting and transporting layer, if necessary, and an electron injecting and transporting layer, if necessary; and further forming a cathode, using the materials and methods described above. Alternatively, the foregoing components may be formed in the reverse order starting from the cathode to the anode to thus form an organic EL device.

Hereinafter, an example of a method for preparing an organic EL device having, in order, anode/hole injecting layer/emitting layer/electron injecting layer/cathode on a light-transmissive substrate will be described.

First of all, a thin film consisting of an anode material is formed on an appropriate light-transmissive substrate at a thickness of 1 $\mu$m or less and preferably 10 to 200 nm using the evaporation method or the sputtering method to thus give an anode. Then a hole injecting layer is formed on said anode. The hole injecting layer can be formed using the vacuum evaporation, spin coating, cast coating or LB method as has been previously described, but the hole injecting layer is preferably formed using the vacuum evaporation method since a uniform film is easily obtained and the formation of any pinhole is inhibited etc. When a hole injecting layer is formed using the vacuum evaporation method, the conditions for the evaporation may vary depending on the kind of compounds used (materials for hole injecting layer) and the crystalline structure and recombined structure of the intended hole injecting layer, but generally, the vacuum evaporation method is preferably carried out under the following conditions: the temperature of the evaporation source: 50 to 450° C.; the degree of vacuum: $10^{-7}$ to $10^{-3}$ Torr; the evaporation rate: 0.01 to 50 nm/sec; the substrate temperature: −50 to 300° C.; the film thickness: 5 nm to 5 $\mu$m.

Subsequently, an emitting layer is applied onto the hole injecting layer. The emitting layer may likewise be prepared by forming a desired organic emitting material into a thin film using the vacuum evaporation, sputtering, spin coating or cast coating method, but the emitting layer is preferably formed using the vacuum evaporation method since a uniform film is easily obtained and the formation of any pinhole is inhibited etc. When an emitting layer is formed using the vacuum evaporation method, the conditions for the evaporation may vary depending on the kind of compounds used, but generally, said conditions can be selected from the same conditions as those of the hole injecting layer.

Next, an electron injecting layer is formed on the emitting layer. The electron injecting layer is preferably formed using the vacuum evaporation method since a uniform film should be formed, like the foregoing hole injecting layer and the emitting layer. The conditions for the evaporation can be selected from the same conditions as those of the hole injecting layer and the emitting layer.

The azaaromatic compound having the azafluoranthene skeleton according to the present invention may be co-evaporated together with other materials when using the vacuum evaporation method, depending upon whether the azaaromatic compound is incorporated into the emitting zone, electron injecting zone or the electron transporting zone. Moreover, when using the spin coating method, other materials can be incorporated into the layer by blending the same with the compound of the invention.

Finally, a cathode is laminated to thus form an organic EL device.

The cathode is a layer consisting of a metal and accordingly, it can be formed using the evaporation method or the sputtering method. However, preferably used herein is the vacuum evaporation technique for the purpose of protecting the underlying organic layers from being damaged during the cathode forming step.

It is preferable that the production steps of the organic EL device are continuously carried out from the anode to the cathode, through a single vacuuming.

The method for forming each layer constituting the organic EL device of the present invention is not restricted to any specific one. Any conventionally known one such as the vacuum evaporation method and the spin coating method can be used. The organic thin film layer containing the compound represented by the foregoing general formula (1) used in the organic EL device of the present invention can be formed using any known film-forming method such as the vacuum evaporation method, the molecular beam evaporation method (MBE method), or the dip coating method, the spin coating method, the cast coating method, the bar coating method or the roll coating method using a solution of said compound in a solvent.

The thickness of each organic layer of the organic EL device according to the present invention is not restricted to any specific level, but if the organic layer is in general too thin, the resulting layer is subjected to defects such as pinholes, while if it is too thick, the resulting EL device requires the application of a high electric voltage for the operation thereof and thus the efficiency thereof is reduced. For these reasons, usually, the thickness thereof preferably ranges from several nanometers to 1 μm.

In this connection, when applying a DC voltage to the organic EL device, a voltage ranging from 5 to 40 V is applied while the polarity of the anode is made positive and that of the cathode is made negative so that the emission of light can be observed. On the other hand, any electric current never flows through the device even when an electric voltage is applied thereto, in case where it is applied in such a condition that the polarities of the electrodes are reversed and accordingly, there is not observed any emitted light. In addition, when applying an alternating voltage to the device, there is observed uniform emission at an instance only when the anode is positively polarized, while the cathode is negatively polarized. The alternating current to be applied to the device may have any wave form.

(Application of Organic EL Device)

The organic EL device of the present invention can be applied to any article which should have a high luminance and a high luminous efficiency even at a low applied electric voltage. For instance, the organic EL device of the invention can be applied to display equipments, displays, lighting equipments, light sources for printers, and backlighting devices for liquid crystal display equipments and the EL device can likewise be used in the fields of signals, advertising displays, and the interior. The display equipment includes a flat panel display which would permit the energy saving and/or ensure a high visibility. In addition, the light source for the printers includes a light source for laser beam printers. Further, the use of the device of the present invention permits the considerable reduction of the volume of the equipment. In respect of the lighting equipments and backlighting devices, it would be expected to achieve an energy saving effect through the use of the device of the present invention.

The present invention will hereunder be described in more detail with reference to the following Examples, but the present invention is by no means limited to these specific Examples.

EXAMPLE

Synthesis Example 1

Synthesis of Compound (12)

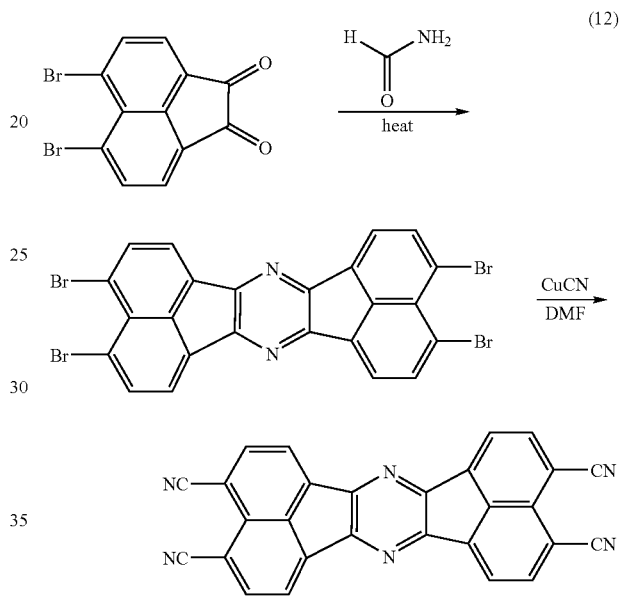

70 ml of formamide was added to 10 g (29 mmol) of 5,6-dibromoacenaphthenequinone and then the reaction was continued at 180° C. for 5 hours. After the completion of the reaction, the resulting solids were recovered by filtration and recrystallized using nitrobenzene. The resulting crystals were recovered by filtration, they were then washed with a small quantity of ethanol, and vacuum-dried at 50° C. to obtain 3.3 g (5.1 mmol) of tetra-(bromoacenaphtheno)pyrazine (yield: 18%). Then the whole of the resulting compound and 2.4 g (26 mmol) of copper cyanide were refluxed in 20 ml of dimethylformamide for 5 hours. After the completion of the reaction, the reaction product was poured into 100 ml of an aqueous solution of ethylenediamine (ethylenediamine:water=3:1) and extracted with dichloromethane, thereafter the extract was washed in order with a 10% aqueous solution of sodium cyanide and a 10% aqueous solution of sodium thiosulfate, and then the resulting organic phase was dried over magnesium sulfate. After the filtration, the concentration and the column purification, 1.4 g (3.3 mmol) of the desired compound (12) were obtained (yield: 65%). This compound was further purified by the sublimation purification technique to use it in the production of an intended device.

FD Mass Spectroscopic Analysis: 428 ($M^+$, bp); HPLC Purity: 98.9%

Synthesis Example 2

Synthesis of Compound (1)

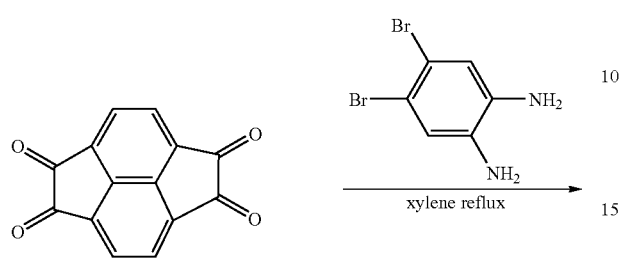

(Intermediate (1-1))

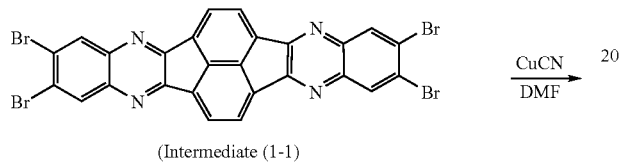

(1)

Cyclopenta[fg]acenaphthylen-1,2,5,6-tetraone (5.0 g, 21 mmol) and 4,5-dibromobenzene-1,2-diamine (14 g, 53 mmol) were refluxed for 8 hours in 150 ml of xylene. After the completion of the reaction, an organic phase was extracted with dichloromethane and washed with a saturated common salt solution, and then the resulting organic phase was dried over magnesium sulfate. After the filtration, the evaporation of the solvent and the column purification, 4.8 g (6.9 mnol) of the intermediate (1-1) were obtained (yield: 33%). Then the whole of the resulting intermediate (1-1) and 5 equivalents of copper cyanide were refluxed in 20 ml of dimethylformamide for 5 hours, as in the Synthesis Example 1. After the completion of the reaction, the reaction product was poured into 100 ml of an aqueous solution of ethylenediamine (ethylenediamine:water=3:1) and extracted with dichloromethane, thereafter the extract was washed in order with a 10% aqueous solution of sodium cyanide and a 10% aqueous solution of sodium thiosulfate, and then the resulting organic phase was dried over magnesium sulfate. After the filtration, the concentration and the column purification, 1.8 g (3.8 mmol) of the intended compound (1) were obtained (yield: 55%). This compound was further purified by the sublimation purification technique to use it in the production of an intended device.

FD Mass Spectroscopic Analysis: 480 ($M^+$, bp);
HPLC Purity: 99.3%

Synthesis Example 3

Synthesis of Compound (4)

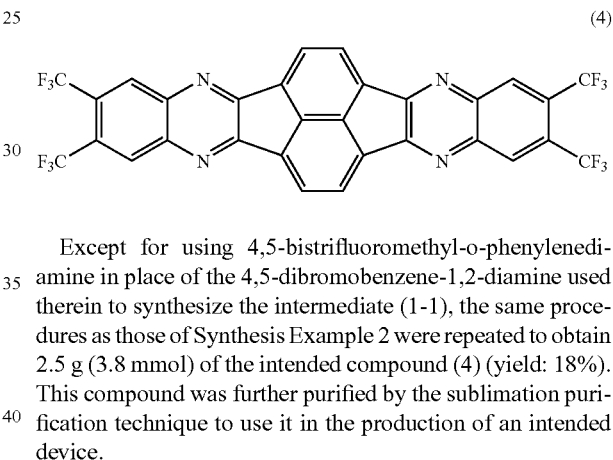

(4)

Except for using 4,5-bistrifluoromethyl-o-phenylenediamine in place of the 4,5-dibromobenzene-1,2-diamine used therein to synthesize the intermediate (1-1), the same procedures as those of Synthesis Example 2 were repeated to obtain 2.5 g (3.8 mmol) of the intended compound (4) (yield: 18%). This compound was further purified by the sublimation purification technique to use it in the production of an intended device.

FD Mass Spectroscopic Analysis: 652 ($M^+$, bp);
HPLC Purity: 99.0%

Synthesis Example 4

Synthesis of Compound (41)

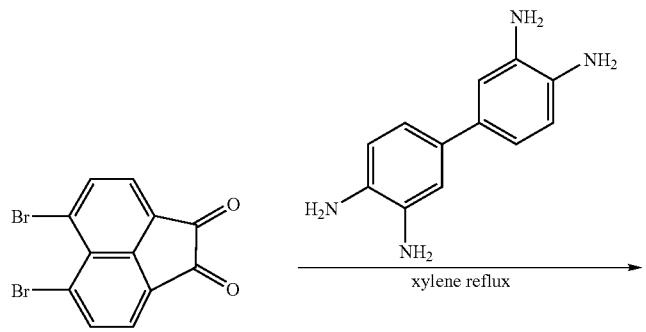

-continued

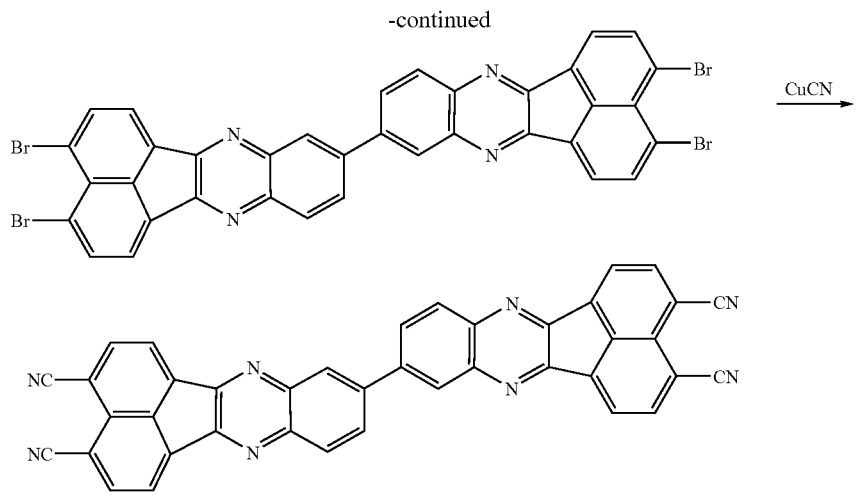

10 g (29 mmol) of 5,6-dibromoacenaphthenequinone and 2.8 g (13 mmol) of 3,3'-diaminobenzidine were refluxed for 12 hours in 120 ml of xylene. After the completion of the reaction, the organic phase was extracted with dichloromethane and washed with a saturated common salt solution, and the resulting organic phase was then dried over magnesium sulfate. After the removal of the magnesium sulfate through filtration, the solvent was distilled off and the resulting residue was subjected to column purification to obtain 5.4 g (6.6 mmol) of a tetrabromo derivative (intermediate) (yield: 51%). Then the whole of the resulting intermediate and 5 equivalents of copper cyanide were refluxed in 20 ml of dimethylformamide for 5 hours, as in the Synthesis Example 1. After the completion of the reaction, the reaction product was poured into 100 ml of an aqueous solution of ethylenediamine (ethylenediamine:water=3:1) and extracted with dichloromethane, thereafter the extract was washed in order with a 10% aqueous solution of sodium cyanide and a 10% aqueous solution of sodium thiosulfate, and then the resulting organic phase was dried over magnesium sulfate. After the filtration, the concentration and the column purification, 1.0 g (1.7 mmol) of the desired compound (41) were obtained (yield: 26%). This compound was further purified by the sublimation purification technique to use it in the production of an intended device.

FD Mass Spectroscopic Analysis: 606 (M$^+$, bp);
HPLC Purity: 99.2%

Synthesis Example 5

Synthesis of Compound (36)

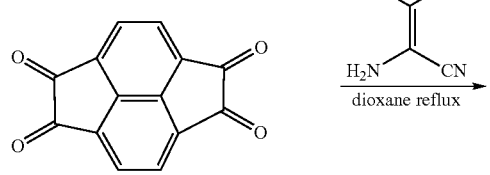

-continued

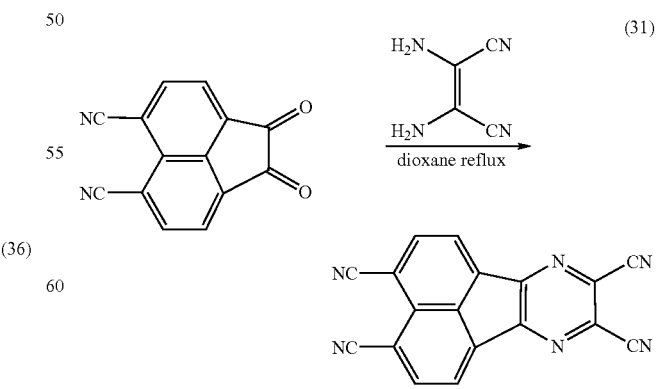

Cyclopenta[fg]acenaphthylen-1,2,5,6-tetraone (4.0 g, 17 mmol) and diaminomaleonitrile (4.4 g, 40 mmol) were refluxed in 100 ml of dioxane. After 8 hours, the reaction was terminated, the solvent was distilled off and the resulting residue was subjected to column purification to obtain 1.8 g (4.7 mmol) of the intended compound (36) (yield: 28%). The resulting compound was further purified by the sublimation purification technique to use it in the production of an intended device.

FD Mass Spectroscopic Analysis: 380 (M$^+$, bp);
HPLC Purity: 99.4%

Synthesis Example 6

Synthesis of Compound (31)

5,6-Dicyanoacenaphthenequinone (8 g, 34 mmol) and diaminomaleonitrile (3.9 g, 36 mmol) were refluxed in 100 ml of dioxane. After 8 hours, the reaction was terminated, the solvent was distilled off and the resulting residue was subjected to column purification to obtain 2.3 g (7.6 mmol) of the intended compound (31) (yield: 23%).

FD Mass Spectroscopic Analysis: 304 (M⁺, bp);
HPLC Purity: 99.4%

Synthesis Example 7

Synthesis of Compound (46)

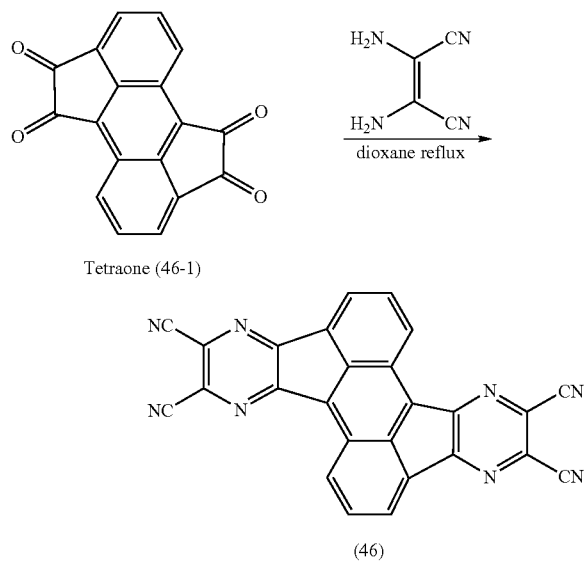

Tetraone (46-1)

(46)

Tetraone (46-1) (6 g, 21 mmol) and diaminomaleonitrile (4.9 g, 45 mmol) were refluxed in 120 ml of dioxane. After 10 hours, the reaction was terminated, the solvent was distilled off and the resulting residue was subjected to column purification to obtain 2.6 g (6.0 mmol) of the intended compound (46) (yield: 29%). The resulting compound was further purified by the sublimation purification technique to use it in the production of an intended device.

FD Mass Spectroscopic Analysis: 430 (M⁺, bp);
HPLC Purity: 99.1%

Synthesis Example 8

Synthesis of Compound (47)

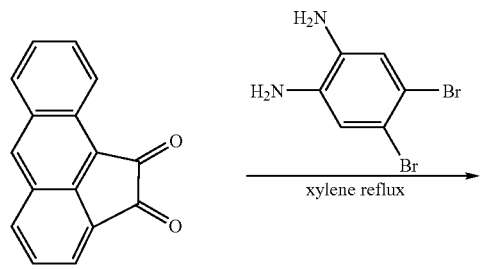

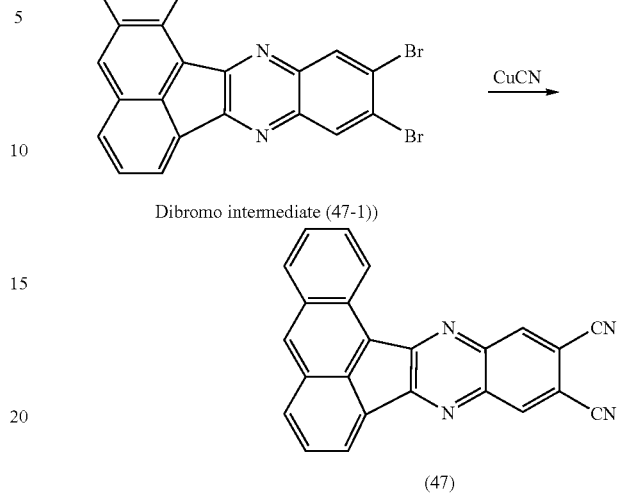

Dibromo intermediate (47-1))

(47)

Aceanthren-1,2-dione (5.0 g, 22 mmol) and 4,5-dibromobenzene-1,2-diamine (7 g, 27 mmol) were refluxed in 150 ml of xylene for 8 hours. After the completion of the reaction, the organic phase was extracted with dichloromethane and washed with an aqueous saturated common salt solution, and the resulting organic phase was then dried over magnesium sulfate. After the filtration, the removal of the solvent through distillation and the column purification, 6.2 g (13 mmol) of a dibromo intermediate (47-1) were obtained (yield: 59%). Then the whole of the resulting dibromo intermediate (47-1) and 3 equivalents of copper cyanide were refluxed in 20 ml of dimethylformamide for 5 hours, as in the Synthesis Example 1. After the completion of the reaction, the reaction product was poured into 100 ml of an aqueous solution of ethylenediamine (ethylenediamine:water=3:1) and extracted with dichloromethane, thereafter the extract was washed in order with a 10% aqueous solution of sodium cyanide and a 10% aqueous solution of sodium thiosulfate, and then the resulting organic phase was dried over magnesium sulfate. After the filtration, the concentration and the column purification, 3.1 g (8.8 mmol) of the intended compound (47) were obtained (yield: 68%).

FD Mass Spectroscopic Analysis: 354 (M⁺, bp);
HPLC Purity: 98.6%

Synthesis Example 9

Synthesis of Compound (48) and Compound (49)

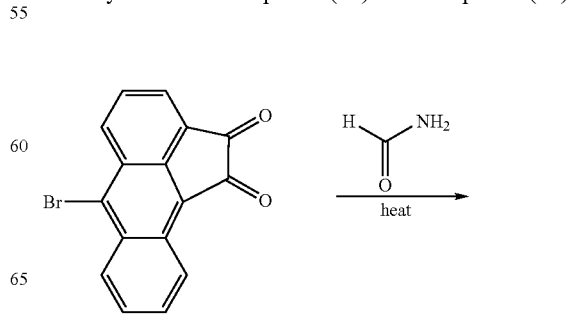

-continued

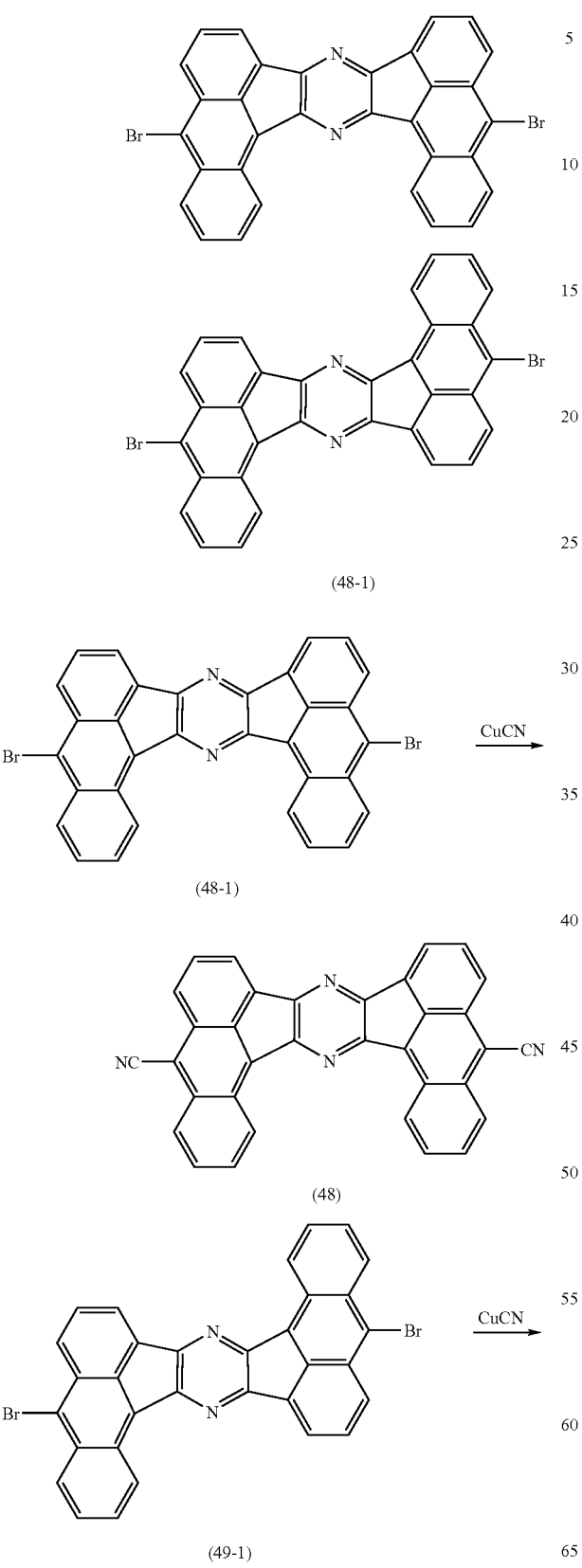

(48-1)

(48-1)

(48)

(49-1)

-continued

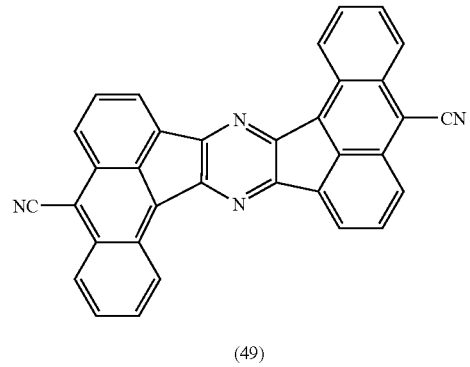

(49)

70 ml of formamide was added to 8.0 g (26 mmol) of 6-bromoaceanthren-1,2-dione and they were reacted at 180° C. for 8 hours. After the completion of the reaction, the organic phase was extracted with dichloromethane and washed with a common salt solution, the resulting organic phase was dried and the solvent was distilled off. Each isomer was separated from impurities using silica gel chromatography to obtain two kinds of isomeric intermediates (48-1) and (49-1) in amounts of 2.6 g (4.8 mmol) and 2.2 g (3.8 mmol), respectively (yield: 8.2 mmol in total, 32%).

Then the whole of the resulting compound (48-1) and 1.1 g (12 mmol) of copper cyanide were refluxed in 18 ml of dimethylformamide for 5 hours. After the completion of the reaction, the reaction product was poured into 100 ml of an aqueous solution of ethylenediamine (ethylenediamine:water=3:1) and extracted with dichloromethane, thereafter the extract was washed in order with a 10% aqueous solution of sodium cyanide and a 10% aqueous solution of sodium thiosulfate, and then the resulting organic phase was dried over magnesium sulfate. After the filtration, the concentration and the column purification, 1.6 g (3.3 mmol) of the intended compound (48) were obtained (yield: 65%).

The resulting compound was further purified by the sublimation purification technique and then used in the production of an intended device.

Then the whole of the resulting intermediate (49-1) and 1.0 g (10 mmol) of copper cyanide were refluxed in 18 ml of dimethylformamide for 5 hours. After the completion of the reaction, the reaction product was poured into 100 ml of an aqueous solution of ethylenediamine (ethylenediamine:water=3:1) and extracted with dichloromethane, thereafter the extract was washed in order with a 10% aqueous solution of sodium cyanide and a 10% aqueous solution of sodium thiosulfate, and then the resulting organic phase was dried over magnesium sulfate. After the filtration, the concentration and the column purification, 1.2 g (2.5 mmol) of the intended compound (48) were obtained (yield: 66%).

FD Mass Spectroscopic Analysis: 478 ($M^+$, bp);

HPLC Purity: 98.9%

Synthesis Example 10

Synthesis of Compound (50)

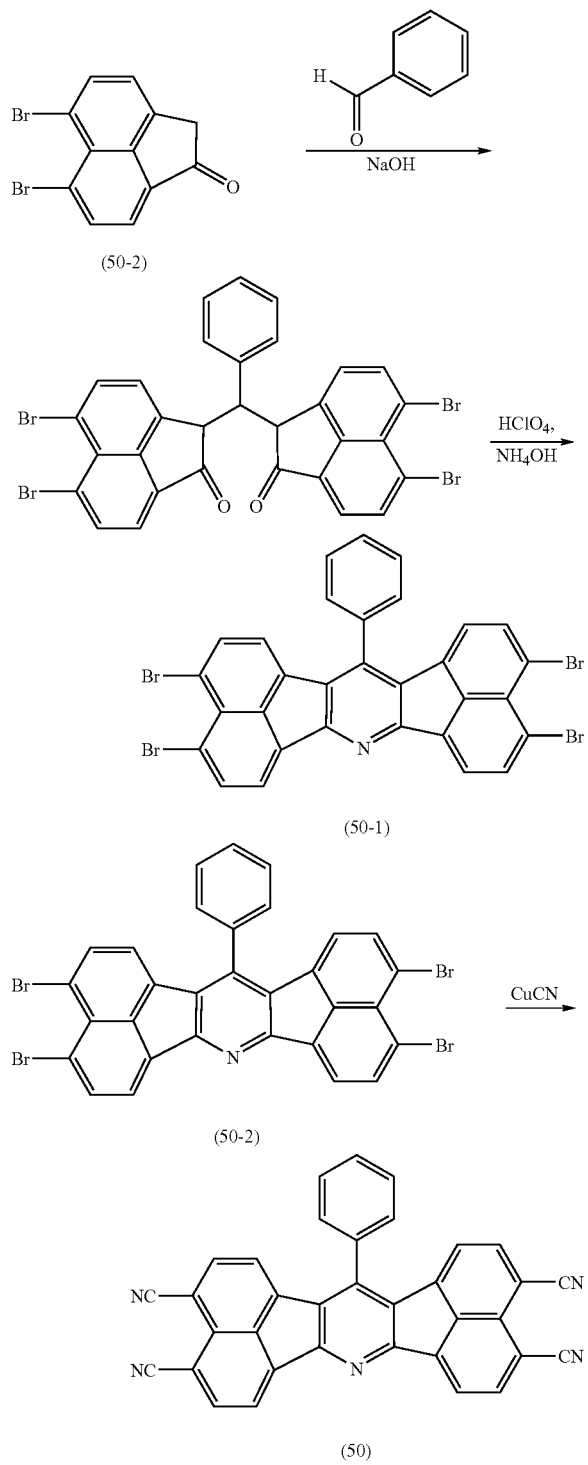

The title compound was synthesized according to the method similar to that disclosed in YAKUGAKU ZASSI, 1969, 89(6): 789. More specifically, 16 g (50 mmol) of 5,6-dibromo-1-acenaphthenone and 2.2 g (20 mmol) of benzaldehyde were dissolved in 180 ml of ethanol, several drops of a 0.1 N aqueous sodium hydroxide solution were added thereto at room temperature with stirring and the resulting mixture was further stirred for additional 2 hours. The solvent was distilled off and the resulting residue was purified using silica gel (chromatography) to obtain 6.2 g (8.4 mmol) of a tetrabromo intermediate (50-1). The whole amount of the intermediate (50-1) was dissolved in 10 ml of $HClO_4$, the resulting solution was heated in a hot water bath for 30 minutes and then cooled to room temperature, 200 ml of acetone was added thereto, an excess of aqueous ammonia was then added thereto, the mixture was warmed and the solvent was distilled off while reducing the pressure.

After the column purification, 19 g (2.7 mmol) of the intermediate (50-2) were obtained. Then the same procedures as those of Example 1 were repeated to synthesize the compound (50). More specifically, the whole of the resulting intermediate (50-2) and 5 equivalents of copper cyanide were refluxed in 20 ml of dimethylformamide for 7 hours. After the completion of the reaction, the reaction product was poured into 100 ml of an aqueous solution of ethylenediamine (ethylenediamine:water=3:1) and extracted with dichloromethane, thereafter the extract was washed in order with a 10% aqueous solution of sodium cyanide and a 10% aqueous solution of sodium thiosulfate, and then the resulting organic phase was dried over magnesium sulfate. After the filtration, the concentration and the column purification, 820 mg (1.6 mmol) of the intended compound (50) were obtained (yield: 59%).

FD Mass Spectroscopic Analysis: 503 ($M^+$, bp);

HPLC Purity: 99.1%

(Preparation of Organic EL Device):

Example 1

ITO/Compound (12)/NPD/Alq/LiF/Al

A glass substrate (a size of 25 mm×75 mm×0.7 mm thick) covered with an ITO transparent electrode was ultrasonically washed in isopropyl alcohol for 5 minutes and then washed with UV ozone for 30 minutes. After the washed glass substrate covered with the transparent electrode was put on a substrate holder of a vacuum deposition equipment, a film of the compound (12) was first formed on the side of the substrate covered with the transparent electrode, in a thickness of 20 nm, in such a manner that the transparent electrode was covered with the film. This film of the compound (12) would serve as a hole injecting layer. Subsequently, a film of a hole transport compound: NPD detailed below was formed on the film of the compound (12) in a thickness of 60 nm. The resulting NPD film would serve as a hole transporting layer. Further, a film of tris(8-quinolinol)aluminum (hereunder referred to as "Alq film") was formed on the NPD film in a thickness of 40 nm. This Alq film would serve as an emitting layer. Thereafter, lithium fluoride was vacuum-deposited in a thickness of 0.1 nm and then aluminum was vacuum-deposited in a thickness of 150 nm. The resulting Al/LiF would serve as a cathode. Metal Al was then vacuum-deposited on the foregoing film to form a metal cathode and thus an organic EL device was completed. The resulting device could emit green light having the following characteristic properties at a direct current voltage of 3.5V: a luminance of emitted light of 130 $cd/m^2$; a current density of 2.4 $mA/cm^2$; and a luminous efficiency of 5.4 cd/A.

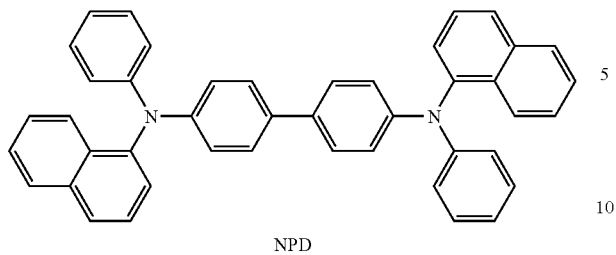

NPD

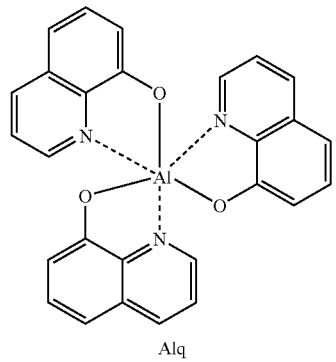

Alq

Example 2

ITO/Compound (36)/NPD/Alq/LiF/Al

The title organic EL device was prepared by repeating the same procedures as those of Example 1 except for using the compound (36) in place of the compound (12).

Example 3

ITO/Compound (1)/NPD/Alq/LiF/Al

The title organic EL device was prepared by repeating the same procedures as those of Example 1 except for using the compound (1) in place of the compound (12).

Example 4

ITO/Compound (46)/NPD/Alq/LiF/Al

The title organic EL device was prepared by repeating the same procedures as those of Example 1 except for using the compound (46) in place of the compound (12).

Comparative Example 1

ITO/CuPc/NPD/Alq/LiF/Al

The title organic EL device was prepared by repeating the same procedures as those of Example 1 except for using the following compound: CuPc in place of the compound (12):

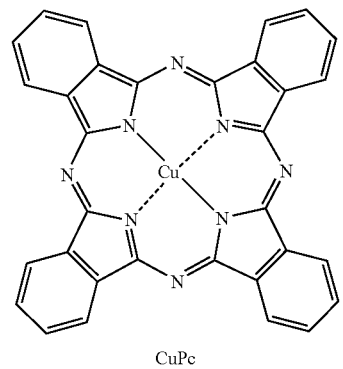

CuPc

Comparative Example 2

ITO/Compound (A)/NPD/Alq/LiF/Al

The title organic EL device was prepared by repeating the same procedures as those of Example 1 except for using the following compound (A) in place of the compound (12):

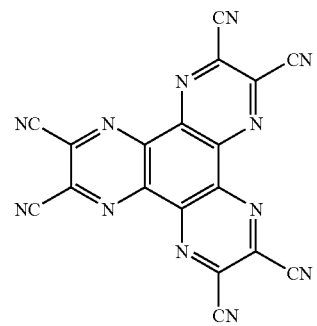

Compound (A)

The results obtained about these Examples and Comparative Examples are listed in the following Table 1:

TABLE 1

| Example No. | Hole injecting material | Voltage (V) | Current Density (mA/cm$^2$) | Luminance (cd/m$^2$) | Luminous Efficiency (cd/A) |
|---|---|---|---|---|---|
| 1 | (12) | 3.5 | 2.4 | 130 | 5.4 |
| 2 | (36) | 3.3 | 2.1 | 122 | 5.8 |
| 3 | (1) | 3.6 | 2.5 | 100 | 4.0 |
| 4 | (46) | 3.3 | 1.9 | 113 | 5.9 |
| 1* | CuPc | 5.5 | 3.2 | 101 | 3.2 |
| 2* | Compound (A) | 4.1 | 2.6 | 102 | 3.9 |

*Comparative Example

Example 5

ITO/Compound (36)/NPD/Compound (B):Irppy 3/BAlq/Alq/LiF/Al

A glass substrate (a size of 25 mm×75 mm×0.7 mm thick) covered with an ITO transparent electrode was ultrasonically washed in isopropyl alcohol for 5 minutes and the washed with UV ozone for 30 minutes. After the washed glass substrate covered with the transparent electrode was put on the substrate holder of a vacuum deposition equipment, a film of the compound (36) was first formed on the side of the substrate covered with the transparent electrode, in a thickness of 20 nm, in such a manner that the transparent electrode was covered with the film. This film of the compound (36) would serve as a hole injecting layer. Subsequently, a film of NPD detailed below was formed on the film of the compound (36) in a thickness of 60 nm. The resulting NPD film would serve as a hole transporting layer. Further, the following compound (B) as a host material was vacuum-deposited on the NPD film in a thickness of 30 nm to form an emitting layer. At the same time, the foregoing metal complex compound Irppy 3 was added to the emitting layer as a phosphorescent Ir metal complex dopant. The concentration of the metal complex compound: Irppy 3 in the emitting layer was set at a level of 7.5% by mass. This film would serve as an emitting layer. Then a film of a compound: BAlq detailed below was formed on the emitting layer in a thickness of 25 nm. This BAlq film would serve as an electron transporting layer. Subsequently, a film of Alq detailed below was formed on the BAlq film in a thickness of 5 nm. This Alq film would serve as an electron injecting layer. Thereafter, lithium fluoride was vacuume-deposited in a thickness of 0.1 nm and then aluminum was vacuume-deposited in a thickness of 150 nm. The resulting Al/LiF would serve as a cathode. In this way an organic EL device was prepared.

The resulting device was sealed and then supplied to the test for electrically charging the device and as a result, it could emit green light having the following characteristic properties at a voltage of 3.3 V and a current density of 0.26 mA/cm$^2$: a luminance of emitted light of 116 cd/m$^2$; and a luminous efficiency of 44.6 cd/A.

Compound (B)

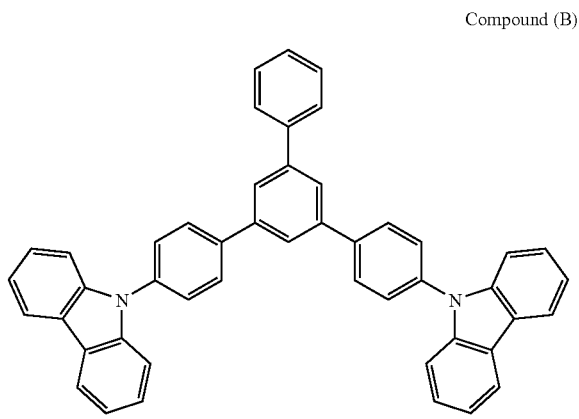

Comparative Example 3

ITO/CuPc/NPD/Compound (B):Irppy 3/BAlq/Alq/LiF/Al

The title organic EL device was prepared by repeating the same procedures as those of Example 5 except for using the compound: CuPc in place of the compound (36). The qualities of the resulting devices obtained are listed in the following Table 2:

TABLE 2

| Example No. | Hole injecting material | Voltage (V) | Current Density (mA/cm$^2$) | Luminance (cd/m$^2$) | Luminous Efficiency (cd/A) |
|---|---|---|---|---|---|
| 5 | (36) | 3.3 | 0.26 | 116 | 44.6 |
| 3* | CuPc | 5.5 | 0.38 | 101 | 26.6 |

*Comparative Example

Example 6

ITO/Compound (41)/TCTA/Compound (C): FIrppy 3/Compound (D)/Alq/LiF/Al

A glass substrate (a size of 25 mm×75 mm×0.7 mm thick) covered with an ITO transparent electrode was ultrasonically washed in isopropyl alcohol for 5 minutes and then washed with UV ozone for 30 minutes. After the washed glass substrate covered with the transparent electrode was put on the substrate holder of a vacuum deposition equipment, a film of the compound (41) was first formed on the side of the substrate covered the transparent electrode, in a thickness of 45 nm, in such a manner that the transparent electrode was covered with the film. This film of the compound (41) would serve as a hole injecting layer. Subsequently, a film of TCTA detailed below was formed on the film of the compound (41) in a thickness of 20 nm. The resulting TCTA film would serve as a hole transporting layer. Further, the compound (C) detailed below serving as a host material was vacuume-deposited on the TCTA film in a thickness of 30 nm to form a emitting layer. At the same time, the foregoing metal complex compound Irppy 3 was added to the emitting layer as a phosphorescent Ir metal complex dopant. The concentration of the metal complex compound: Irppy 3 in the emitting layer was set at a level of 8% by mass. This film would serve as an emitting layer. Then a film of a compound (D) detailed below was formed on the emitting layer in a thickness of 25 nm. This film of the compound (D) would serve as an electron transporting layer. Subsequently, a film of the compound Alq was formed on the film of the compound (D) in a thickness of 5 nm. This Alq film would serve as an electron injecting layer. Thereafter, lithium fluoride was vacuume-deposited on the electron injecting layer in a thickness of 0.1 nm and then aluminum was vacuume-deposited in a thickness of 150 nm. The resulting Al/LiF would serve as a cathode. In this way an organic EL device was prepared.

The resulting device was sealed and then supplied to the test for electrically charging the device and as a result, it could emit green light having the following characteristic properties at a voltage of 3.8 V and a current density of 0.25 mA/cm$^2$: a luminance of emitted light of 104 cd/m$^2$; and a luminous efficiency of 41.6 cd/A.

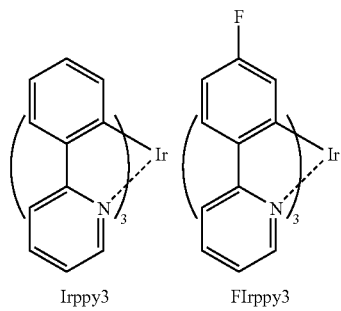

Irppy3    FIrppy3

-continued

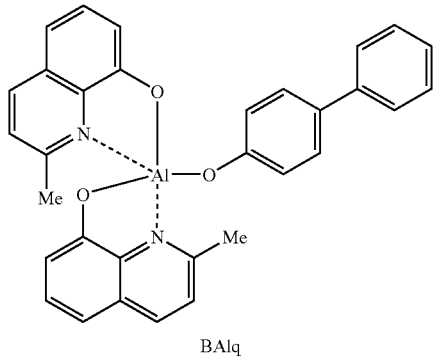

BAlq

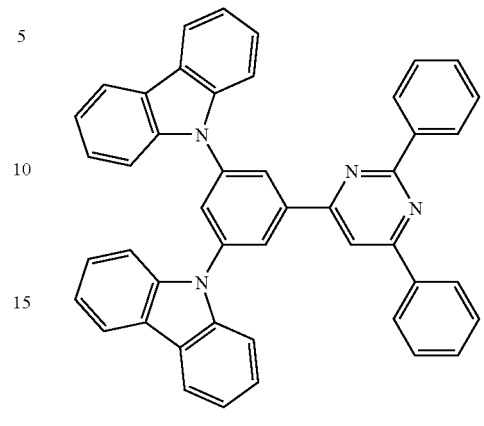

Compound (D)

Comparative Example 4

An organic EL device was prepared by repeating the same procedures as those of Example 6 except for using the compound (A) in place of the compound (41). The qualities of the resulting devices obtained are listed in the following Table 3:

TABLE 3

| Example No. | Hole injecting material | Voltage (V) | Current Density (mA/cm$^2$) | Luminance (cd/m$^2$) | Luminous Efficiency (cd/A) |
|---|---|---|---|---|---|
| 6 | (41) | 3.8 | 0.25 | 104 | 41.6 |
| 4* | Compound (A) | 4.7 | 0.36 | 106 | 29.4 |

*Comparative Example

The organic EL device prepared in Examples 1 to 5 using the metal complex compounds according to the present invention can be operated at a low voltage and have high luminous efficiency as compared with the organic EL device prepared in Comparative Examples 1 to 3.

As has been described above in detail, the organic EL device prepared using the metal complex compounds according to the present invention shows a high luminous efficiency and a long lifetime, can be used as a material for organic EL devices capable of emitting light of a variety of colors including blue, and can be applied to various fields such as a variety of display devices, displays, backlighting devices, light sources for illumination, signals, advertising displays, and the interior, and in particular, the device is suitable for use as a display device of color displays.

TCTA

Compound (C)

What is claimed is:

1. An azaaromatic compound having an azafluoranthene skeleton represented by the following general formula (3):

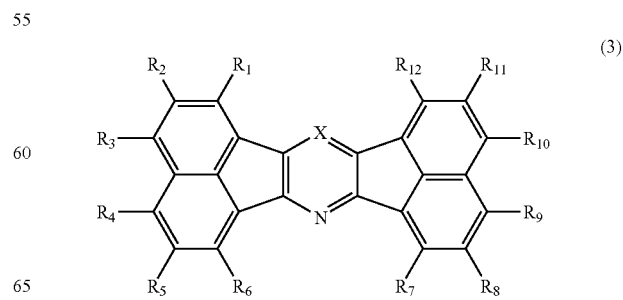

(3)

wherein

x is C/N, C($R_{13}$) or N, $R_1$ to $R_{13}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{13}$ each represent a cyano group, a trifluoromethyl group or a fluorine atom and that those of $R_1$ to $R_{13}$, which are adjacent to one another, may be linked together to form a ring structure.

2. An azaaromatic compound having an azafluoranthene skeleton represented by the following general formula (5) or (5'):

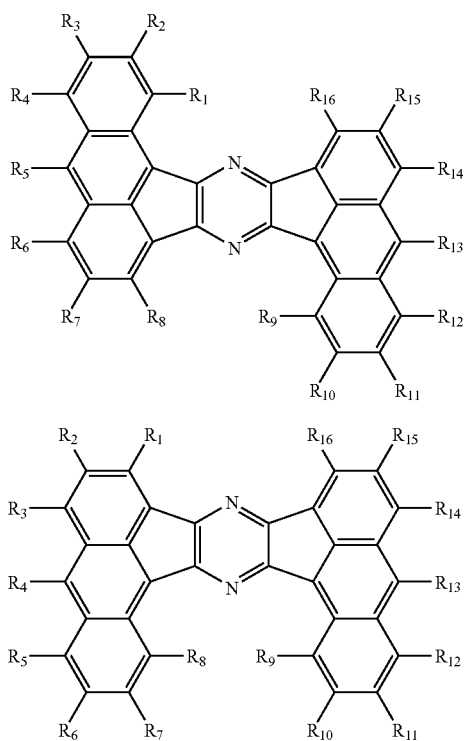

wherein $R_1$ to $R_{16}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{16}$ each represent a cyano group, a trifluoromethyl group or a fluorine atom and that those of $R_1$ to $R_{16}$, which are adjacent to one another, may be linked together to form a ring structure.

3. An azaaromatic compound according to claim 1 having an azafluoranthene skeleton represented by the following general formula (6):

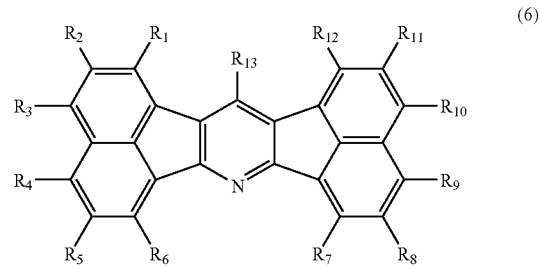

wherein $R_1$ to $R_{13}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{13}$ each represent a cyano group, a trifluoromethyl group or a fluorine atom and that those of $R_1$ to $R_{13}$, which are adjacent to one another, may be linked together to form a ring structure.

4. An azaaromatic compound having an azafluoranthene skeleton represented by the following general formula (8):

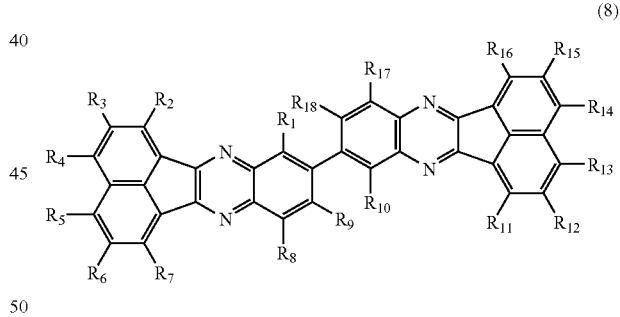

wherein $R_1$ to $R_{18}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 40 carbon atoms, a trialkylsilyl group wherein the alkyl group has 1 to 20 carbon atoms and may have a substituent, an aryloxy group wherein the aryl group has 6 to 40 carbon atoms and may have a substituent, a halogen atom, or a cyano group, provided that at least two of $R_1$ to $R_{18}$ each represent a cyano group, a trifluoromethyl group or a fluorine atom and that those of $R_1$ to $R_{18}$, which are adjacent to one another, may be linked together to form a ring structure.

5. A material for organic electroluminescence devices comprising the azaaromatic compound having the azafluoranthene skeleton of claim 1.

6. A hole injecting or hole transporting material for organic electroluminescence devices comprising the azaaromatic compound having the azafluoranthene skeleton of claim 1.

7. An electron injecting or electron transporting material for organic electroluminescence devices comprising the azaaromatic compound having the azafluoranthene skeleton of claim 1.

8. An organic electroluminescence device which comprises one or a plurality of organic layers which are interposed between a cathode and an anode, wherein at least one of the organic layers comprises the azaaromatic compound having the azafluoranthene skeleton of claim 1.

9. The organic electroluminescence device according to claim 8, wherein the organic layer comprising the azaaromatic compound having the azafluoranthene skeleton is a hole injecting or hole transporting layer.

10. The organic electroluminescence device according to claim 8, wherein the organic layer comprising the azaaromatic compound having the azafluoranthene skeleton is an electron injecting or electron transporting layer.

11. The organic electroluminescence device according to claim 8, wherein the azaaromatic compound having the azafluoranthene skeleton is an azaaromatic compound to which 4 cyano groups are linked.

12. The organic electroluminescence device according to claim 8, wherein the device comprises a layer of an inorganic compound between at least one of the electrodes and the organic layer.

13. The organic electroluminescence device according to claim 8, wherein the device comprises an emitting layer comprising a phosphorescent compound.

14. An equipment comprising the organic electroluminescence device according to claim 8.

15. An organic electroluminescence device which comprises one or a plurality of organic layers which are interposed between a cathode and an anode, wherein at least one of the organic layers comprises the azaaromatic compound having the azafluoranthene skeleton of claim 2.

16. An organic electroluminescence device which comprises one or a plurality of organic layers which are interposed between a cathode and an anode, wherein at least one of the organic layers comprises the azaaromatic compound having the azafluoranthene skeleton of claim 3.

17. An organic electroluminescence device which comprises one or a plurality of organic layers which are interposed between a cathode and an anode, wherein at least one of the organic layers comprises the azaaromatic compound having the azafluoranthene skeleton of claim 4.

18. The azaaromatic compound as claimed in claim 1, wherein x is N.

19. The azaaromatic compound as claimed in claim 2, having an azafluoranthene skeleton represented by general formula (5).

20. The azaaromatic compound as claimed in claim 2, having an azafluoranthene skeleton represented by general formula (5').

* * * * *